United States Patent
Khanna

(10) Patent No.: US 9,693,805 B2
(45) Date of Patent: Jul. 4, 2017

(54) DECOMPRESSIVE CRANIOTOMY FIXATION DEVICE

(71) Applicant: Rohit Khanna, Daytona Beach, FL (US)

(72) Inventor: Rohit Khanna, Daytona Beach, FL (US)

(*) Notice: Subject to any disclaimer, the term of this patent is extended or adjusted under 35 U.S.C. 154(b) by 0 days.

(21) Appl. No.: 14/578,142

(22) Filed: Dec. 19, 2014

(65) Prior Publication Data

US 2015/0238229 A1 Aug. 27, 2015

Related U.S. Application Data

(63) Continuation of application No. 14/269,242, filed on May 5, 2014, now abandoned, which is a continuation of application No. 12/655,280, filed on Dec. 28, 2009, now Pat. No. 8,747,477.

(51) Int. Cl.
  *A61B 17/68* (2006.01)
  *A61B 17/00* (2006.01)

(52) U.S. Cl.
  CPC .. *A61B 17/688* (2013.01); *A61B 2017/00991* (2013.01)

(58) Field of Classification Search
  CPC .............. A61B 17/688; A61B 17/8061; A61B 2017/00991
  See application file for complete search history.

(56) References Cited

U.S. PATENT DOCUMENTS

| | | | | | |
|---|---|---|---|---|---|
| 3,347,575 | A | * | 10/1967 | Morris | F16B 7/105 16/429 |
| 3,964,788 | A | * | 6/1976 | Kmetyko | A47C 7/383 108/149 |
| 5,012,394 | A | * | 4/1991 | Woodward | F21L 4/045 362/198 |
| 5,487,741 | A | * | 1/1996 | Maruyama | A61B 17/8085 606/286 |
| 6,355,036 | B1 | * | 3/2002 | Nakajima | A61B 17/66 606/54 |
| 6,367,339 | B1 | * | 4/2002 | Lilonsky | A01K 89/02 73/828 |
| 2005/0273100 | A1 | * | 12/2005 | Taylor | A61B 17/7035 623/17.11 |
| 2008/0200954 | A1 | * | 8/2008 | Tucci | A61B 17/688 606/280 |

* cited by examiner

*Primary Examiner* — Zade Coley
(74) *Attorney, Agent, or Firm* — Wenderoth, Lind & Ponack, L.L.P.

(57) ABSTRACT

The present invention relates to a craniotomy fixation device and method for fixing a bone flap to the skull following craniotomy. The device may comprise two portions, one portion may be associated with the skull and the other portion may be associated with the bone flap. The two portions are connected in a way to accommodate changes in intracranial pressure.

20 Claims, 40 Drawing Sheets

DECOMPRESSIVE CRANIOTOMY FIXATION DEVICE

This application is a continuation of patent application Ser. No. 14/269,242, filed on May 5, 2014, which is a continuation of patent application Ser. No. 12/655,280, filed on Dec. 28, 2009, and claims priority thereof.

BACKGROUND

Neurosurgery routinely involves performing craniotomies for exposure of the brain and intracranial contents for various intracranial pathologies including tumors, head injuries, vascular malformations, aneurysms, infections, hemorrhages, strokes, and brain swelling. A craniotomy involves creation of burr holes and removal of a portion of the skull (bone flap) with subsequent approximation of the bone flap for closure. Several methods and fixation devices are available for re-attaching the bone flap to the skull including small metallic or absorbable plates with screws or wires as demonstrated in U.S. Pat. No. 5,578,036 to Stone et al., U.S. Pat. No. 5,916,200 to Eppley et al, and U.S. Pat. No. 5,916,217 to Manthrop et al. Another method has been the use of cranial clamps consisting of two connected circular elements placed on the inside and outside surfaces of the skull. Various descriptions of cranial clamps in the art include U.S. Pat. No. 5,707,373 to Sevrain, U.S. Pat. No. 5,800,436 to Lerch, U.S. Pat. No. 6,485,493 to Bremer, U.S. Pat. No. 6,379,363 to Herrington et al., U.S. Pat. No. 6,755,834 to Amis, U.S. Pat. No. 7,048,737 to Wellisz et al., U.S. Pat. No. 7,361,178 to Hearn et al., U.S. Pat. No. 7,387,633 to Ahmad et al., and U.S. Pat. No. 6,685,707 to Roman et al.

All of the aforementioned cranial fixation devices in the prior art provide for a rigid fixation of the bone flap to the skull. In cases of post-operative intracranial hemorrhage and/or brain swelling development, a decompressive craniectomy is performed. Decompressive craniectomy is a neurosurgical procedure used to treat increased intracranial pressure (ICP) from head injury, stroke, brain tumor, infection, cerebral hemorrhage, and space occupying lesions. The technique involves removal of the skull and opening of the dura mater covering the brain, thereby allowing the swollen brain to herniate outwards through the surgical skull defect rather than downwards to compress the brainstem. The procedure improves outcomes by lowering ICP, the pressure within the skull. Increased ICP is very often
debilitating or fatal because it causes compression of the brain and restricts cerebral blood flow. The aim of decompressive craniectomy is to reduce this pressure. The larger the removed bone-flap is, the more ICP is reduced. Following removal of the bone flap, the dural opening is closed with a patch graft taken from a cow, pig, cadaver, or a synthetic graft. The preferred method is a synthetic collagen matrix since it is capable of expanding. In addition to reducing ICP, studies have found decompressive craniectomy to improve cerebral perfusion pressure and cerebral blood flow in head injured patients. Decompressive craniectomy is used to treat major strokes associated with malignant brain swelling and increased ICP. It is well known that a decompressive craniectomy improves survival and functional outcome in patients with severe brain swelling from head injury or stroke if performed in a timely manner. There usually is an inherent time delay between diagnosing the cause of the increased intracranial pressure and performing the decompressive craniectomy. Typically, once a post-operative increase in ICP is detected, either through a clinical exam or an ICP monitoring device, medical treatment is initiated and aCT or MRI imaging is obtained to identify the underlying cause of the raised intracranial pressure. If the need for a re-operation or decompressive cranlectomy is identified, the anesthesiologist and operating room staff are notified and the surgery is subsequently undertaken. Unfortunately, at times the operating room and/or staff are at full capacity necessitating further delay until the surgery can be performed. Despite the best of attempts by the surgeon, in cases of massive brain swelling or a rapidly developing post-operative hemorrhage, the patient may end up with irreversible brainstem injury with consequent vegetative state or death.

After a craniectomy, the risk of brain injury is increased because of the removed bone flap, particularly after the patient heals and becomes mobile again. There is also a very obvious cosmetic skin deformity. Therefore, special measures must be taken to protect the brain, such as a helmet or a temporary implant in the skull. Other risks include infection, cerebrospinal fluid leakage, hydrocephalus, encephalomyocele, subdural hygroma and hemorrhage.

When the patient has healed sufficiently, the craniectomy skull defect is usually closed with a cranioplasty. Cranioplasty is repair of a defect in the vault of the skull. This repair can be carried out by using bone removed at earlier surgery that has been preserved or by using bone from elsewhere as a graft. The iliac bone bounding the pelvis, ribs and even a part of adjacent skull bone can be used.

If possible, the original bone flap is preserved after the cranlectomy in anticipation of the cranioplasty. The bone flap is usually stored sterilely in a freezer until the patient is ready for implantation of the bone flap into the cranlectomy skull defect. Typically, this time period can last several months since it may take this long to treat the underlying cause of the Increased intracranial pressure. This extended time period not only increases the risk of brain injury but also increases the risk of Infection in the stored bone flap. Another technique of storing the removed bone flap involves placing it under the skin in the abdomen. This requires a surgical procedure to place the bone flap in the abdomen and another one to remove it, thereby also increasing the consequent risks to the patient. In cases where the bone flap cannot be replaced due to infection or any other reason, the skull defect is repaired either with a prosthetic plate or a titanium mesh and bone cement. A prosthesis obviously cannot completely replicate the original skull defect and therefore, some cosmetic deformity persists following a prosthetic cranioplasty. The prosthesis also increases the risk of infection.

The risks associated with cranioplasty include infection, hemorrhage, brain injury, seizures, and death along with other risks inherent to any surgery and general anesthesia. It is also usually necessary for the patient to be in hospital for a week or so after a cranioplasty.

Other cranial fixation devices in the prior art describe their use for distraction osteogenesis. U.S. Pat. No. 5,902,304 to Walker et al. describes a telescopic bone plate for use in bone lengthening by distraction osteogenesis. The bone plates are attached to osteomically separated mandible or skull sections connected by a thread screw assembly. The extent of the required distraction can be adjusted by an external screwdriver. U.S. Pat. No. 5,993,448 to Daniel J. Remmier describes a skull fixation device for treatment of craniofacial deformities that provides for relative movement of the skull segments by a percutaneously placed external wrench, U.S. Pat. No. 6,187,004 to Jeffrey A. Fearon describes a mandible or skull expansion plate. The extent of the expansion is adjusted by an externally placed device.

U.S. Pat. No. 6,355,036 to Nakajima describes skull expansion plates with a hinged plate at one end and a bone adjuster at the other end comprising two plates with a shaft. The shaft has to be operated externally to adjust the distance between the bone flap and skull.

The aforementioned cranial fixation devices in the prior art provide for treatment of craniofacial defects in particular craniosynostosis. They all require an external screwdriver to control the extent of the skull movement allowed and they do not describe or provide for outward or inward movement of the bone flap relative to the skull in response to a change in the intracranial pressure. These devices are also placed on the outer surface of the skull with a very high profile thereby, increasing the risk of painful scalp irritation and palpable cosmetic deformities. Chronic scalp irritation from high profile cranial fixation devices can risk erosion and exposure of the device through the skin with consequent life threatening infection.

U.S. patent application Ser. No. 11/749,990 to Kathryn Ko describes a method of performing decompressive craniectomy with the bone flap attached to the skull with a hinged plate. The method describes attaching the hinged plate to one end of the bone flap and attaching the other end to a rigid plate or no plate at all. The described method also requires a re-operation to fixate the unconstrained bone flap at the rigid plate or plate free end to the skull once the brain swelling subsides. U.S. patent application Ser. No. 12/033,815 to Tucci also describes a method similar to the Ko 11fi49,990 application of attaching the bone flap to the skull with a hinged plate at one end of the bone flap and a straight plate at the other end with unconstrained bone flap movement. Tucci also describes a deformable plate which could be used instead of a hinged plate for bone flap attachment. This construct would also require a re-operation to fixate the unconstrained bone flap at the straight plate end. The hinged plate bone flap end would not be able to move outwards and therefore, allow very limited bone flap movement. Tucci also describes a two part sliding device for cranial fixation. The device is not very practical as it very significantly sticks outwards from the skull surface and has a very high profile and obvious painful cosmetic defect with overlying skin irritation and risk of erosion/infection. Due to the high protuberance, this device would also require another operation to remove it once the bone flap approximates to the skull.

Considering the aforementioned complexities and risks involved in the post-operative management of critically ill patients undergoing a craniotomy, there is a need for a better technique and device which provides for cranial fixation along with immediate treatment of increased intracranial pressure and avoids the need for performing a subsequent cranioplasty.

SUMMARY OF THE INVENTION

The present invention relates to a cranial fixation device for fixing a bone flap to the skull following a craniotomy. It also provides for constrained outward movement of the bone flap to immediately accommodate for an increase in intracranial pressure (ICP) and subsequently allowing for the bone flap to move inwards up to the skull once the ICP normalizes.

In one embodiment, the cranial fixation device comprises of two heads with one head attached to the skull and the other to the bone flap. The plates are attached to the skull and bone flap with screws. The telescopic portion slidably connects the two heads and is positioned in the skull burr hole defect. The telescopic portion allows outward movement of the bone flap as well as inward movement of the bone flap up to the skull level and does not allow the bone flap to move inward inside the cranium below the skull level.

An increase in ICP can result from several pathologies including traumatic injury, stroke, hypoxia, hypertension, brain tumor, aneurysm, arteriovenous malformation, infection, venous sinus thrombosis, craniosynostosis, and hydrocephalus. Traumatic injury can be either closed head injury from blunt trauma or penetrating head injury from a gunshot wound and usually results in development of brain swelling and hemorrhage comprising of subdural hemorrhage, epidural hemorrhage, subarachnoid hemorrhage, intra-ventricular hemorrhage, brain hemorrhage, and cerebral contusions. Strokes can be ischemic, hemorrhagic or a combination of both and usually result from cerebral vessel occlusion. Vessel occlusion can be from an arterial embolus from carotid or vertebral artery stenosis, atrial fibrillation, heart septal defect, heart valve abnormalities, heart or aortic aneurysm surgery, carotid or vertebral artery dissection/thrombosis, and vasculitis. Larger strokes result in the development of severe cerebral cytotoxic edema and brain swelling. Treatment of the strokes with antiplatelet therapy or anticoagulation can also lead to the development of cerebral hemorrhage in some cases, further worsening the brain swelling. Strokes can also be caused by cerebral vessel occlusion from atherosclerotic disease, vasospasm from aneurysmal or traumatic subarachnoid hemorrhage, vasculitis, and a hypercoaguable state. Cerebral venous sinus occlusion can result in significant diffuse brain swelling as well as hemorrhage. Hypertension is a frequent cause of cerebral hemorrhage particularly deep brain and intraventricular hemorrhage. Severe hypertension can also lead to diffuse brain swelling even without any hemorrhage. Hypoxia from cardiac arrest or apnea can lead to diffuse cerebral cytotoxic injury and consequent brain swelling. Ruptured cerebral aneurysms result in subarachnoid hemorrhage but not infrequently also cerebral and intraventricular hemorrhage with associated hydrocephalus which can result in significant and immediate rise in ICP. Ruptured arteriovenous malformation scan also result in cerebral and intraventricular hemorrhage. Some arteriovenous malformations like Vein of Galen aneurysm can enlarge to a significant size leading to a rise in Intracranial pressure without even rupturing.

Brain tumors either metastatic or primary like gliomas and meninglomas, often cause brain swelling from vasogenic edema. Infections include brain abscess, subdural empyema, epidural abscess, and cerebritis can also lead to significant brain swelling. Seizures can lead to diffuse brain swelling from increased cerebral blood flow and metabolism.

When an increase in ICP exceeds the normal range, the bone flap is pushed outwards and places the telescopic portion in an extended position. Once the ICP normalizes, the telescopic portions fall back into a retracted position. The retracted telescopic portion position approximates the two heads and thereby the bone flap and the skull. Typically two more of the cranial fixation devices would be needed to achieve this form of decompressive craniectomy. Alternatively, a cranial fixation device can be placed on one side of the bone flap and a hinge device can be placed on the other side to provide a similar but limited decompressive craniotomy. In another embodiment of the cranial fixation device, the heads are attached to the skull and bone flap with spikes or a combination of screws on one head and spikes on the other. In another embodiment of the cranial fixation device, one or both head comprise of clamps which are attached to the skull and/or bone flap.

In another embodiment, the cranial fixation device telescopic portion comprises a locking mechanism that engages when the telescopic bone fastener is in a retracted position. The retracted telescopic portion position approximates the bone flap to the skull when the intracranial pressure is in the normal range. With an increase in ICP, the pressure placed on the bone flap disengages the telescopic bone fastener locking mechanism and allows outward movement of the bone flap to accommodate the increase in ICP. Subsequently, once the ICP normalizes, the bone flap retracts back to the skull level. The locking mechanism comprises of one or more collapsible balls mounted on one telescopic extension with corresponding sockets on the said second telescopic component. Other locking mechanisms include ratchet teeth, ratchet teeth and pawl mechanism, collapsible ratchet teeth, threads, hook mechanism, and ridges with notches. Several locking mechanisms are described here forth. In one embodiment of the cranial fixation device, the locking mechanism comprises a ridge in one telescopic extension with a corresponding socket or defect in the other telescopic extension. In another embodiment of the cranial fixation device, the locking mechanism comprises of ridges in the telescopic extension with notches in the other telescopic extension. In another embodiment of the cranial fixation device, the locking mechanism comprises of ratchet teeth in the telescopic extensions. In another embodiment of the cranial fixation device, the locking mechanism comprises of ratchet teeth in one telescopic extension with a pawl in the other telescopic extension. The ratchet teeth can be unidirectional or bidirectional. In another embodiment of the cranial fixation device, the locking mechanism comprises of collapsible ratchet teeth in the telescopic extension with an engaging defect or ratchet teeth in the other telescopic extension. In another embodiment of the cranial fixation device, the locking mechanism comprises a hook in one telescopic extension with a corresponding engaging hole in the other telescopic extension.

Rather than providing a fixed locked position once implanted as described in all the cranial fixation devices in the prior art, the current invention allows for constrained outward movement of the bone flap relative to the skull in cases of cerebral swelling and subsequently retracts the bone flap against the skull once the swelling subsides.

In the various embodiments described herein the preferred head configuration is circular or semi-circular so as to cover the burr hole or skull opening. Other plate configurations could be rectangular, square, straight, X-shaped, Y-shaped, fan shaped, or any other configuration able to connect the skull to the bone flap. Similarly, the telescopic configurations described are either cylindrical or rectangular and designed to fit into the skull defect or burr hole. Other telescopic configurations could be partially solid, tapered, V-shaped or any other configuration that fits the skull opening. The positioning of the telescopic portion in the burr hole skull defect provides for a very low profile cranial fixation with no scalp irritation or risk of skin erosion. The cranial fixation device can be made of titanium or titanium alloy for MRI imaging compatibility. They could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the bone flap has fused with the skull. Alternatively, it could be made of a radiolucent material (polyetheretherketone), plastic, or a combination of plastic and metal to reduce CT and MRI imaging artifact.

Although the application for the cranial fixation device described in the various embodiments is for fixation of the bone flap to the skull following a craniotomy and provide for a method of decompressive cranlectomy for treatment of Increased intracranial pressure, it can also be used to cover a burr hole or skull fracture and treat congenital cranial skull defects like craniosynostosis Various embodiments and advantages of the current invention are set forth in the following detailed description and claims which will be readily apparent to one skilled in the art.

DETAILED DESCRIPTION OF THE PREFERRED EMBODIMENTS

Figure 1:
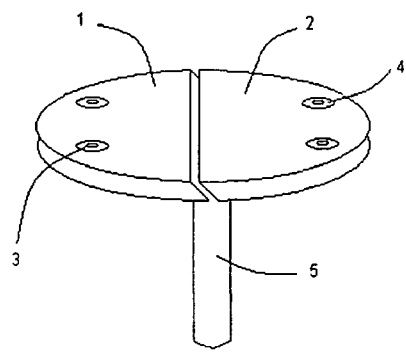
FIG. 1 is a perspective diagram of one embodiment of the cranial fixation device in a retracted position.
Figure 2:
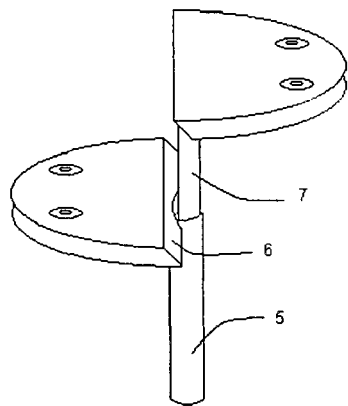
FIG. 2 is a perspective diagram of the device seen in FIG. 1 in an extended position.
Figure 3:
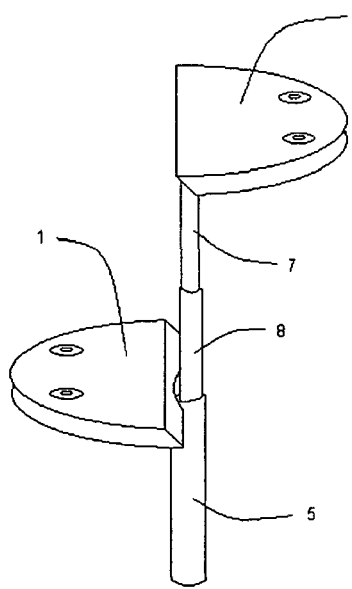
FIG. 3 is a perspective diagram of another embodiment of the cranial fixation device in an extended position.
Figure 4:
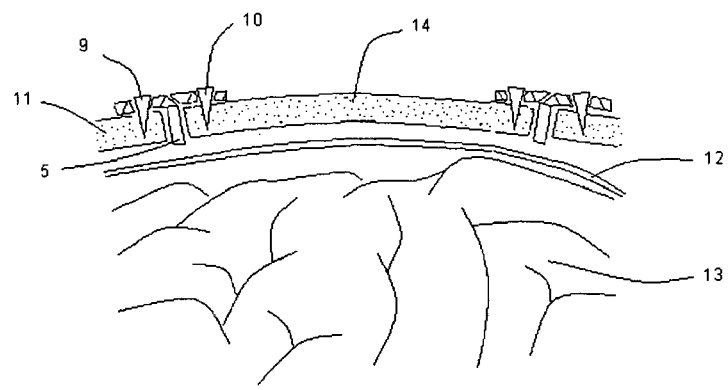
FIG. 4 is a schematic diagram of the cranial fixation device seen in FIG. 1 in a retracted position attached to the skull and bone flap.
Figure 5:
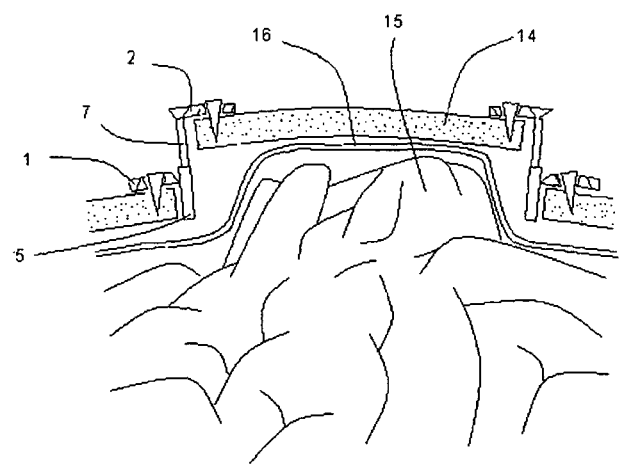
FIG. 5 is a schematic diagram of the device as seen in FIG. 2 in an extended position attached to the skull and bone flap.
Figure 6:
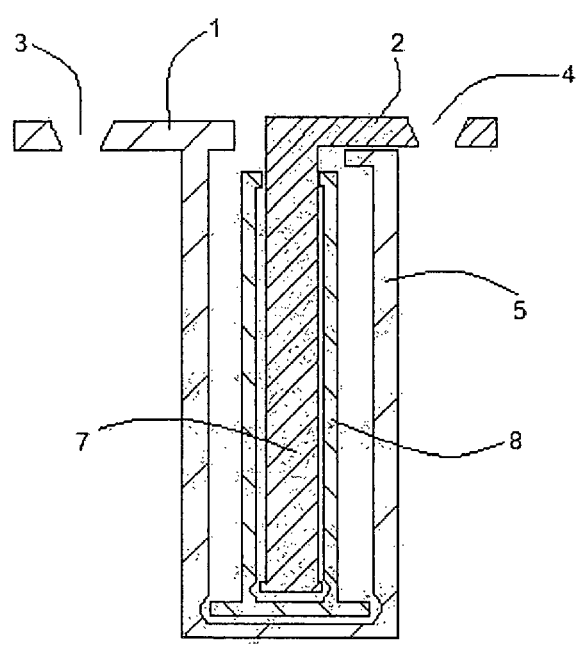
FIG. 6 is a cross-sectional side view of the device seen in FIG. 3 in a retracted position.
Figure 7:
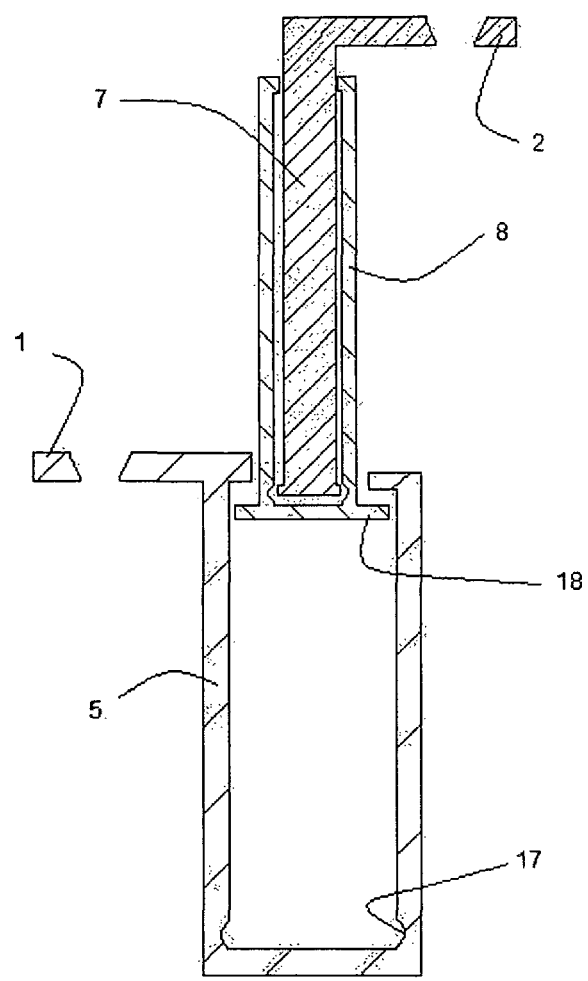
FIG. 7 is a cross-sectional side view of the device seen in FIG. 3 in a partially extended position.
Figure 8:
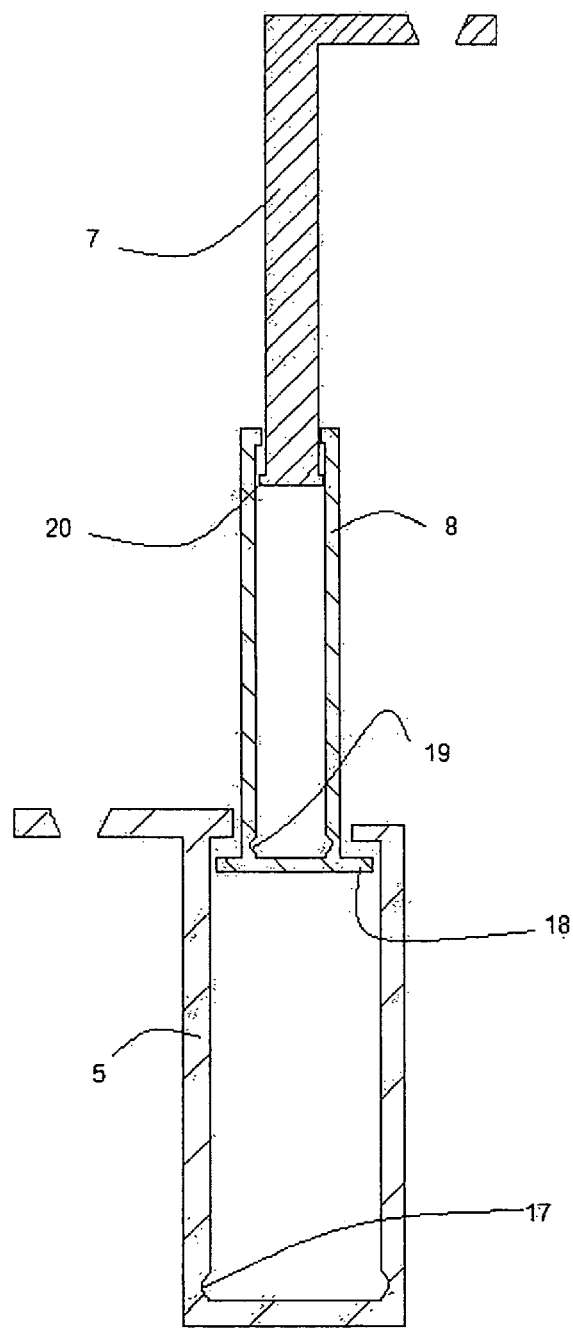
FIG. 8 is a cross-sectional side view of the device seen in FIG. 3 in a completely extended position.

The present invention describes a method for cranial fixation following a craniotomy with the fixation device allowing for constrained movement of the bone flap to accommodate an Increase in Intracranial pressure. The cranial fixation device as shown in FIGS. 1 and 2 comprises of a head 1 with an extension 5 and a head 2 with an extension 7. The extensions 5 and 7 are telescopic and allow for inward or outward movement of the heads relative to each other. The medial edges of the heads 1 and 2 are sloped 6 and overlap each other when the heads are approximated, thereby not allowing the head 2 to move inward beyond the head 1. The head 1 has holes 3 which allows placement of screws attaching the head to the outer surface of the skull. Head 2 has holes 4 through which screws can be placed for attachment of the head to the outer surface of the bone flap. FIG. 1 shows the telescopic extensions in a compressed position whereby extension 5 is contained in the extension 7 and FIG. 2 shows the extensions 5 and 7 in a distracted position. FIG. 3 illustrates another embodiment of the cranial fixation device with an intermediate telescopic component 8 which allows the two heads attached to their respective bone flap and skull to move outwards further if needed to accommodate an increase in intracranial pressure. The method for cranial bone flap fixation with the device in FIGS. 1 and 2 is illustrated in FIGS. 4 and 5. FIG. 4 illustrates the cranial fixation device in place attached to the bone flap 14 with screw 10 and attached to the skull 11 with screw 9. The brain 13 and dura 12 are shown in their normal position. Typically two or more of the cranial fixation devices would be placed to fixate the bone flap 14 to the skull 11 with the cranial fixation device telescopes in a retracted position approximating the bone flap to the skull. As shown in FIG. 5, with the development of brain swelling or an increase in intracranial pressure from a hemorrhage, the brain 15 pushes against the bone flap 14. The pressure on the bone flap places the cranial fixation device telescopes 7 in an extended position thereby allowing the head 2 attached to the bone flap to move outwards relative to the head 1 attached to the skull and accommodate the brain swelling. The dural closure material is preferably a collagen matrix that allows expansion but is not necessary. The dura can be left open or other dural substitutes made from autograft, allograft, or xenograft material can also be used. Once the brain swelling subsides, the bone flap moves back in towards the skull but the overlap of the cranial fixation heads prevents the bone flap from moving inside the skull. FIGS. 6-8 illustrate a cross-sectional view of the cranial fixation device shown in FIG. 3. The head 1 contains a hole 3 for a screw to be placed to secure the head to the skull and a telescopic housing compartment 5 which typically would reside in the skull opening or burr hole defect. The head 2 contains a hole 4 for a screw to be placed into the bone flap and a telescopic extension 7. The intermediate telescopic component 8 resides between the telescopic portions 5 and 7. FIG. 6 shows the cranial fixation device in a retracted position. FIG. 7 shows the device in a partially extended position. The intermediate telescopic component 8 comprises of extension 18 at one end which prevents it from pulling completely out of the housing compartment 5. The housing compartment 5 comprises of a recess 17 at one end which engages with the extension 18 of the telescopic portion 8 in a retracted position to lock these two telescopic portions as illustrated in FIG. 6. FIG. 8 illustrates the device in a completely extended position. The telescopic portion 7 comprises of extension 20 at the end which prevents it from pulling completely out of the telescopic component 8. The telescopic component 8 also comprises of a recess 19 at one end which engages with the extension 20 of the telescopic portion 7 in a retracted position to lock these two telescopic portions as shown in FIG. 6.

Figure 9:
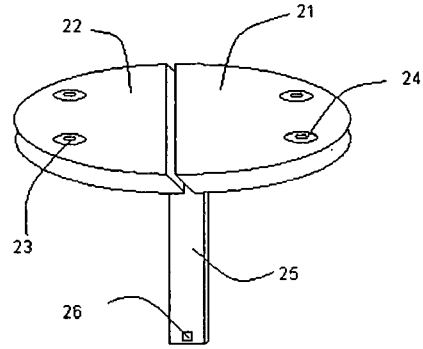
FIG. 9 is a perspective diagram of another embodiment of the cranial fixation device in a retracted position.
Figure 10:
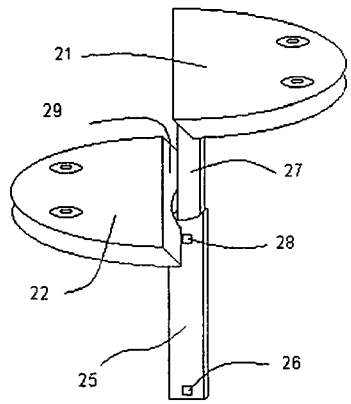
FIG. 10 is a perspective diagram of the device seen in FIG. 9 in an extended position.
Figure 11:
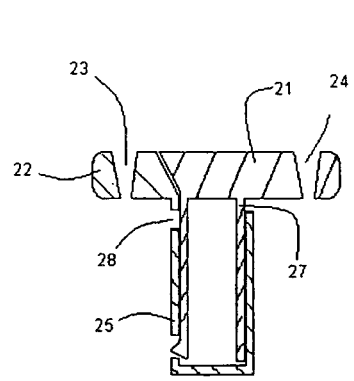
FIG. 11 is a cross-sectional side view of the device seen in FIG. 9.
Figure 12:
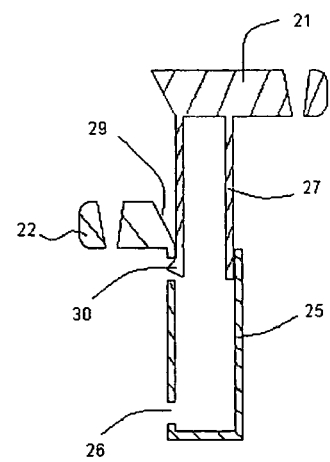
FIG. 12 is a cross-sectional side view of the device seen in FIG. 10.

In another embodiment of the cranial fixation device as shown in FIGS. 9-12, the head 22 comprises an extension 25 and the head 21 comprises an extension 27. The extensions 25 and 27 are telescopic and allow for inward or outward movement of the heads relative to each other. The medial edges of the heads 22 and 24 are sloped 29 and overlap each other when the heads are approximated, thereby not allowing the head 21 to move inward beyond the head 22. The head 22 has holes 23 which allows placement of screws attaching the head to the skull. Head 21 has holes 23 through which screws can be placed for attachment of the head to the bone flap. FIGS. 9 and 11 show the telescopic extensions in a compressed position whereby extension 27 is contained inside the extension 25 and FIGS. 10 and 12 show the extensions 27 and 25 in a distracted position. The telescopic extension 25 also comprises recess 26 and 28 which engage with a ridge 30 on the telescopic extension 27. The recess 26 engages with ridge on the telescopic extension 27 in a completely retracted position and the recess 28 engages with the ridge on the telescopic extension 27 in a completely extended position and therefore prevents the extension 27 from completely pulling out of the extension 25.

Figure 13:
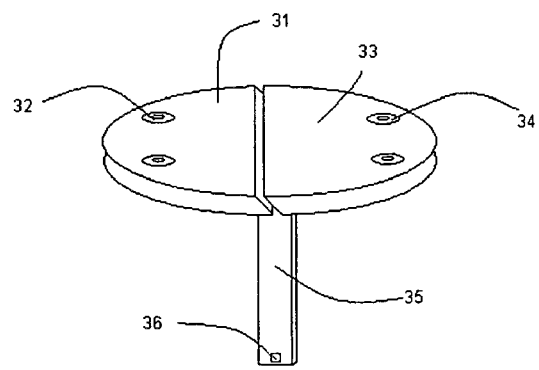
FIG. 13 a perspective diagram of another embodiment of the cranial fixation device in a retracted position.
Figure 14:
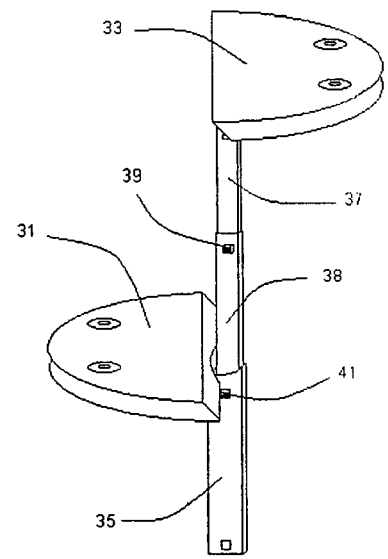
FIG. 14 is a perspective diagram of the device seen in FIG. 13 in an extended position.
Figure 15:
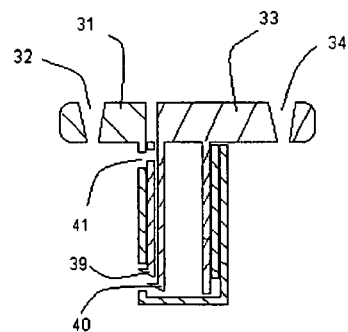
FIG. 15 is a cross-sectional side view of the device seen in FIG. 13.
Figure 16:
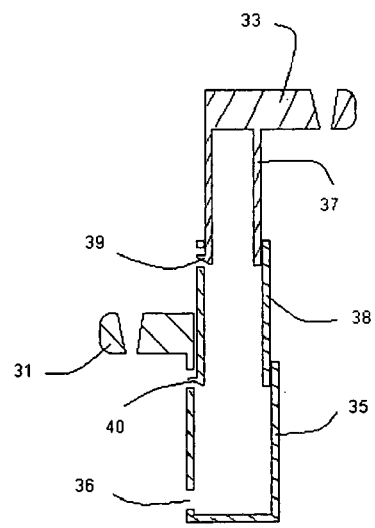
FIG. 16 is a cross-sectional view of the device seen in FIG. 14.

In another embodiment of the cranial fixation device as shown in FIGS. 13-16, the head 31 comprises an extension 35 and the head 33 comprises an extension 37. An intermediate telescopic extension 38 connects the extensions 35 and 37. The telescopic extensions allow for inward or outward movement of the heads relative to each other. The head 31 has holes 32 which allows placement of screws attaching the head to the skull. Head 33 has holes 34 through which screws can be placed for attachment of the head to the bone flap. FIGS. 13 and 15 show the telescopic extensions in a compressed position whereby extensions 37 and 38 are contained inside the extension 35 and FIGS. 14 and 16 show the extensions 37 and 38 in a distracted position. The telescopic extension 35 also comprises recesses 36 and 41 which engage with a ridge 40 on the telescopic extension 38. The recess 36 engages with ridge 40 on the telescopic extension 35 in a completely retracted position and the recess 41 engages with the ridge 40 on the telescopic extension 38 in an extended position and prevents the extension 38 from completely pulling out of the extension 35. The telescopic extension 38 also comprises of a recess which engages a ridge 39 on the telescopic extension 37 in an extended position as shown in FIG. 16. In a retracted position as seen in FIG. 15 the ridge 39 engages with the ridge 40 and maintains the telescopes in that position.

Figure 17:
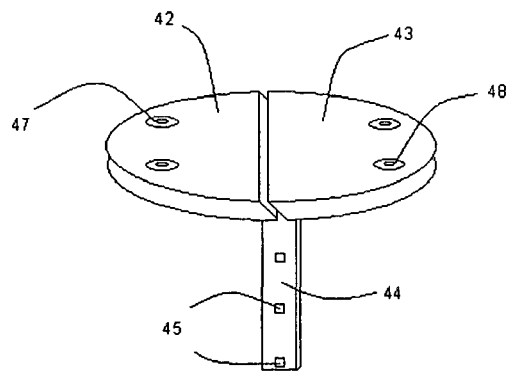
FIG. 17 is a perspective diagram of another embodiment of the cranial fixation device in a retracted position.
Figure 18:
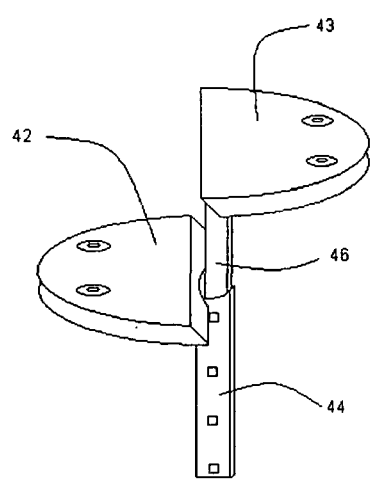
FIG. 18 is a perspective diagram of the device seen in FIG. 17 in an extended position.
Figure 19:
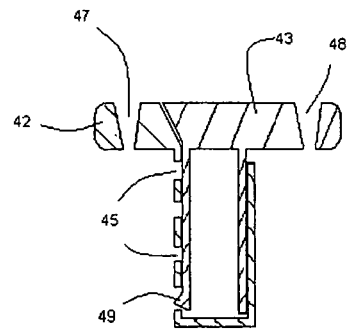
FIG. 19 is a cross-sectional view of the device seen in FIG. 17.
Figure 20:
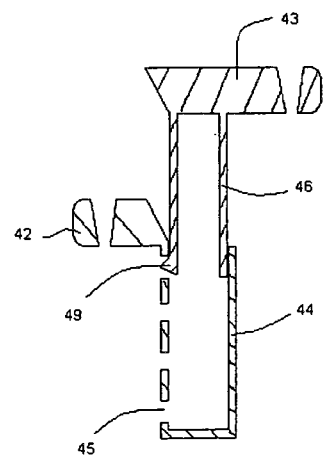
FIG. 20 is a cross-sectional view of the device seen in FIG. 18.

In another embodiment of the cranial fixation device as shown in FIGS. 17-20, the head 42 comprises an extension 44 and the head 43 comprises an extension 46. The extensions 44 and 46 are telescopic and allow for inward or outward movement of the heads relative to each other. The head 42 has holes 47 which allows placement of screws attaching the head to the skull. Head 43 has holes 48 through which screws can be placed for attachment of the head to the bone flap. FIGS. 17 and 19 show the telescopic extensions in a compressed position whereby extension 46 is contained inside the extension 44 and FIGS. 18 and 20 show the extensions 46 and 44 in a distracted position. The telescopic extension 44 also comprises recesses 45 which engage with a ridge 49 on the telescopic extension 46.

Figure 21:
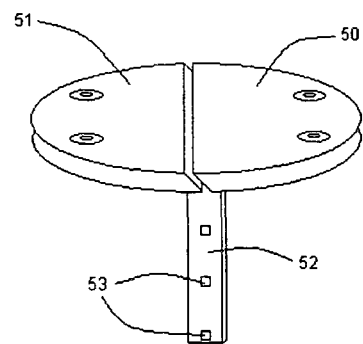
FIG. 21 a perspective diagram of another embodiment of the cranial fixation device in a retracted position.
Figure 22:
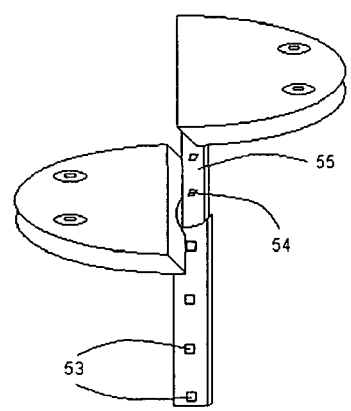
FIG. 22 is a perspective diagram of the device seen in FIG. 21 in an extended position.

In another embodiment of the cranial fixation device as shown in FIGS. 21 and 22, the head 51 comprises an extension 52 and the head 50 comprises an extension 55. The extensions 52 and 55 are telescopic and allow for inward or outward movement of the heads relative to each other. FIG. 21 shows the telescopic extensions in a compressed position whereby extension 55 is contained inside the extension 52 and FIG. 21 shows the extensions 52 and 55 in a distracted position. The telescopic extension 52 also comprises multiple recesses 53 which engage with ridges 54 on the telescopic extension 55.

Figure 23:
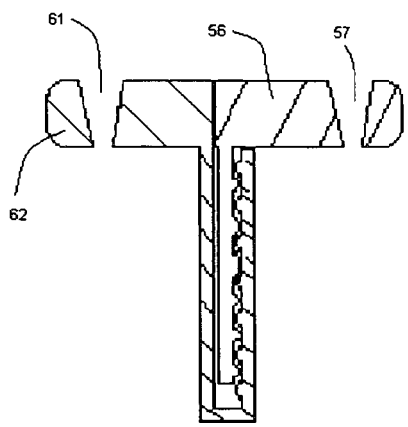
FIG. 23 is a cross-sectional side view of another embodiment of the cranial fixation device in a retracted position.
Figure 24:
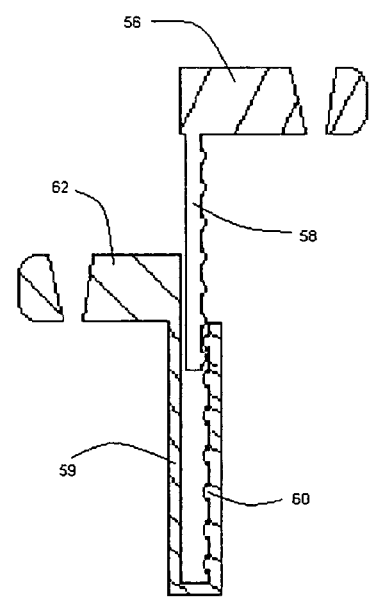
FIG. 24 is a cross-sectional view of the device seen in FIG. 23 in an extended position.

In another embodiment of the cranial fixation device as shown in FIGS. 23 and 24, the head 62 comprises an extension 59 and the head 56 comprises an extension 58. The head 62 has holes 61 which allows placement of screws attaching the head to the skull. Head 56 has holes 57 through which screws can be placed for attachment of the head to the bone flap. The extensions 58 and 59 are telescopic and allow for inward or outward movement of the heads relative to each other. FIG. 23 shows the telescopic extensions in a compressed position whereby extension 58 is contained inside the extension 59 and FIG. 24 shows the extensions 58 and 59 in a distracted position. The telescopic extension 58 also comprises multiple ridges which engage with ridges 60 in the telescopic extension 59.

Figure 25:
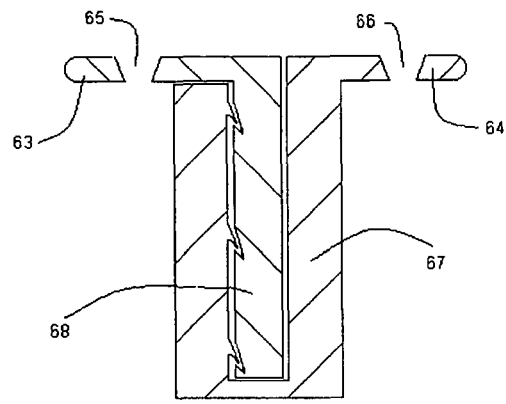
FIG. 25 is a cross-sectional side view of another embodiment of the cranial fixation device in a retracted position.
Figure 26:
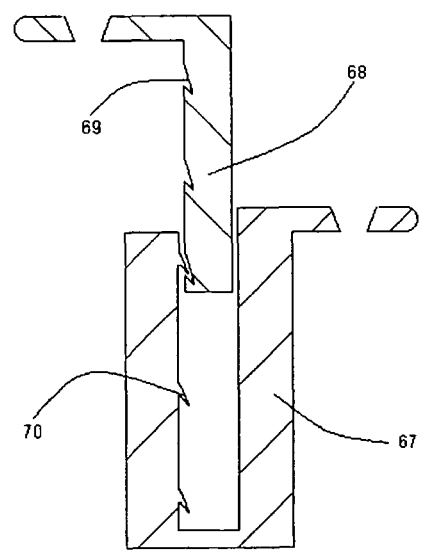
FIG. 26 is a cross-sectional view of the device seen in FIG. 25 in an extended position.

In another embodiment of the cranial fixation device as shown in FIGS. 25 and 26, the head 63 comprises an extension 68 and the head 64 comprises an extension 67. The head 64 has holes 66 which allows placement of screws attaching the head to the skull. Head 63 has holes 65 through which screws can be placed for attachment of the head to the bone flap. The extensions 67 and 68 are telescopic and allow for inward or outward movement of the heads relative to each other. FIG. 25 shows the telescopic extensions in a compressed position whereby extension 68 is contained inside the extension 67 and FIG. 26 shows the extensions 67 and 68 in a distracted position. The telescopic extension 68 also comprises multiple ratchet teeth recesses 69 which engage with the ratchet teeth 70 in the telescopic extension 67.

Figure 27:
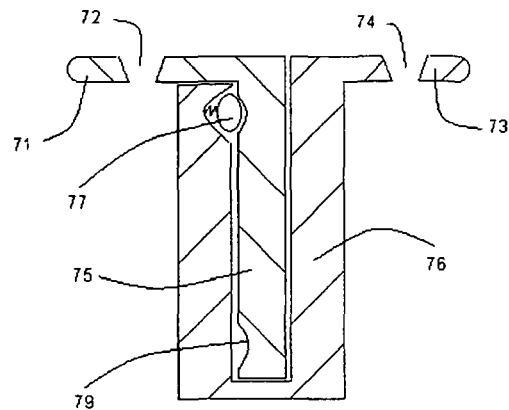
FIG. 27 is a cross-sectional side view of another embodiment of the cranial fixation device in a retracted position.
Figure 28:
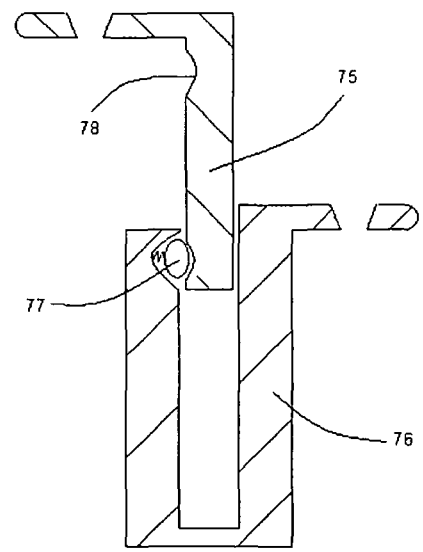
FIG. 28 is a cross-sectional view of the device seen in FIG. 27 in an extended position.

In another embodiment of the cranial fixation device as shown in FIGS. 27 and 28, the head 71 comprises an extension 75 and the head 73 comprises an extension 76. The head 73 has holes 74 which allows placement of screws attaching the head to the skull. Head 71 has holes 72 through which screws can be placed for attachment of the head to the bone flap. The extensions 75 and 76 are telescopic and allow for inward or outward movement of the heads relative to each other. The telescopic extension 75 also comprises sockets 78 and 79 which engage with the collapsible ball mechanism 77 in the telescopic extension 78. FIG. 27 shows the telescopic extensions in a compressed position with ball 77 engaged with the socket 78 and extension 75 contained inside the extension 76. FIG. 28 shows the extensions 75 and 76 in a distracted position with the ball 77 engaged with socket 79.

Figure 29:
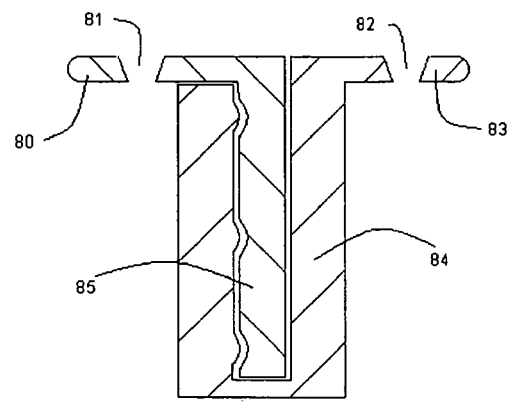
FIG. 29 is a cross-sectional side view of another embodiment of the cranial fixation device in a retracted position.
Figure 30:
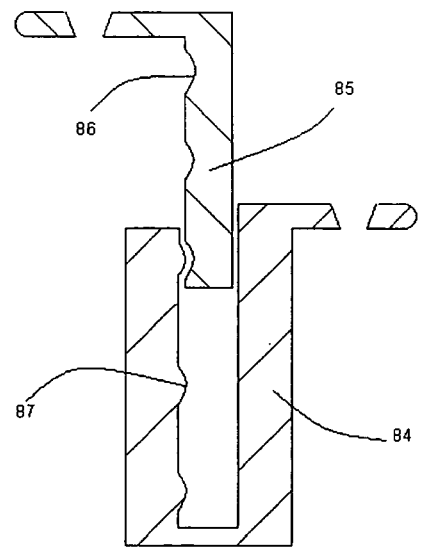
FIG. 30 is a cross-sectional view of the device seen in FIG. 29 in an extended position.

In another embodiment of the cranial fixation device as shown in FIGS. 29 and 30, the head 80 comprises an extension 85 and the head 83 comprises an extension 84. The head 83 has holes 82 which allows placement of screws attaching the head to the skull. Head 80 has holes 81 through which screws can be placed for attachment of the head to the bone flap. The extensions 84 and 85 are telescopic and allow for inward or outward movement of the heads relative to each other. The telescopic extension 85 also comprises sockets 86 which engage with the ridges 87 in the telescopic extension 84. FIG. 29 shows the telescopic extensions in a compressed position with the ridges 87 engaged with the sockets 86 and extension 85 contained inside the extension 84. FIG. 30 shows the extensions 85 and 86 in a distracted position.

Figure 31:
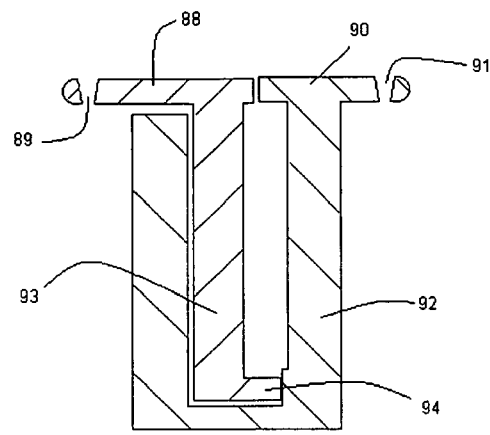
FIG. 31 is a cross-sectional side view of another embodiment of the cranial fixation device in a retracted position.
Figure 32:
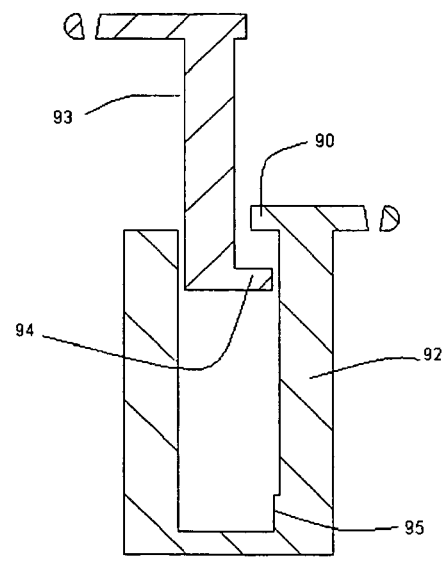
FIG. 32 is a cross-sectional view of the device seen in FIG. 31 in an extended position.

In another embodiment of the cranial fixation device as shown in FIGS. 31 and 32, the head 88 comprises an extension 93 and the head 90 comprises an extension 92. The head 90 has holes 91 which allows placement of screws attaching the head to the skull. Head 88 has holes 89 through which screws can be placed for attachment of the head to the bone flap. The extensions 92 and 93 are telescopic and allow for inward or outward movement of the heads relative to each other. The telescopic extension 93 also comprises an extension 94 at one end. The telescopic component 92 has an extension 95 at one end. FIG. 31 shows the telescopic extensions 92 and 93 in a compressed position with their respective extensions 95 and 94 engaged. FIG. 32 shows the extensions 92 and 93 in a distracted position with the extension 94 preventing the head 88 and extension 93 from pulling out of the telescopic component 92.

Figure 33:
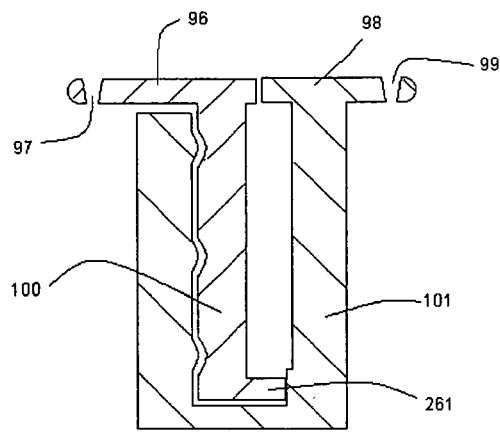
FIG. 33 is a cross-sectional side view of another embodiment of the cranial fixation device in a retracted position.
Figure 34:
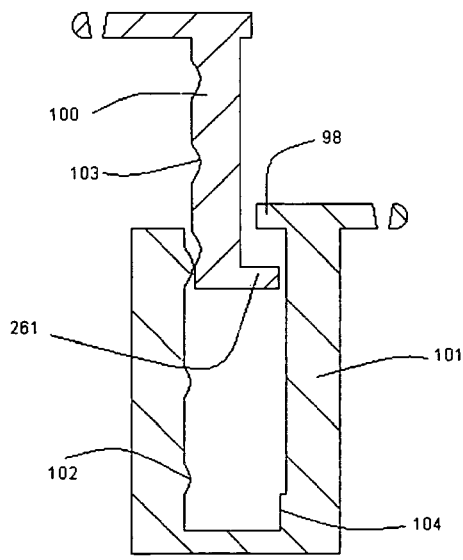
FIG. 34 is a cross-sectional view of the device seen in FIG. 33 in an extended position.

In another embodiment of the cranial fixation device as shown in FIGS. 33 and 34, the head 98 comprises an extension 101 and the head 96 comprises an extension 100. The head 98 has holes 99 which allows placement of screws attaching the head to the skull. Head 96 has holes 97 through which screws can be placed for attachment of the head to the bone flap. The extensions 100 and 101 are telescopic and allow for inward or outward movement of the heads relative to each other. The telescopic extension 100 also comprises an extension 261 at one end and sockets 103 along the body. The telescopic component 101 has an extension 104 at one end and ridges 102 along the body. FIG. 33 shows the telescopic extensions 100 and 101 in a compressed position with their respective extensions 104 and 261 engaged. The ridges 102 are also shown engaged with the recesses 103. FIG. 34 shows the extensions 100 and 101 in a distracted position with the extension 261 preventing the head 96 and extension 100 from pulling out of the telescopic component 101.

Figure 35:
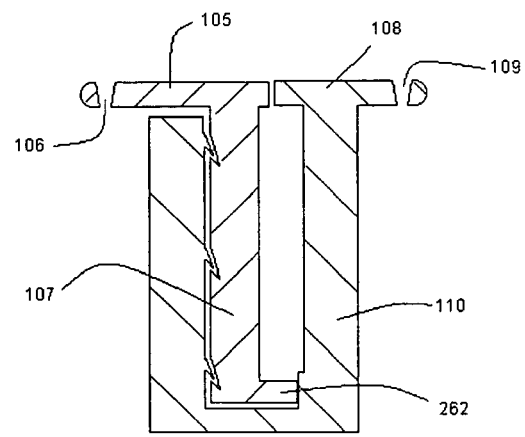
FIG. 35 is a cross-sectional side view of another embodiment of the cranial fixation device in a retracted position.
Figure 36:
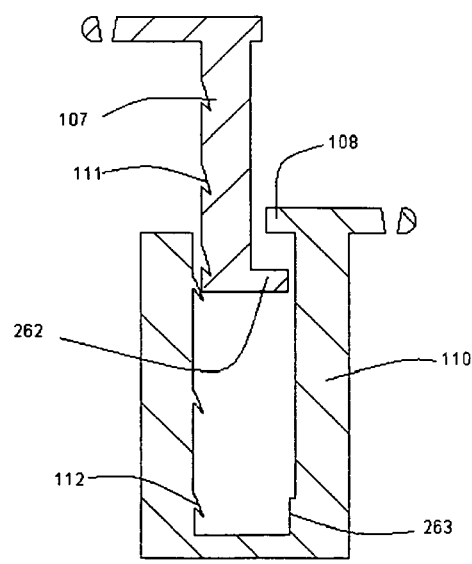
FIG. 36 is a cross-sectional view of the device seen in FIG. 35 in an extended position.

In another embodiment of the cranial fixation device as shown in FIGS. 35 and 36, the head 108 comprises an extension 1.10 and the head 105 comprises an extension 107. The head 108 has holes 109 which allows placement of screws attaching the head to the skull. Head 105 has holes 106 through which screws can be placed for attachment of the head to the bone flap. The extensions 107 and 110 are telescopic and allow for inward or outward movement of the heads relative to each other. The telescopic extension 107 also comprises an extension 262 at one end and ratchet teeth recesses 111 along the body. The telescopic component 110 has an extension 263 at one end and ratchet teeth 112 along the body. FIG. 35 shows the telescopic extensions 107 and 110 in a compressed position with their respective extensions 262 and 263 engaged. FIG. 35 shows the extensions 107 and 110 in a distracted position with the extension 262 preventing the extension 107 from pulling out of the telescopic component 110.

Figure 37:
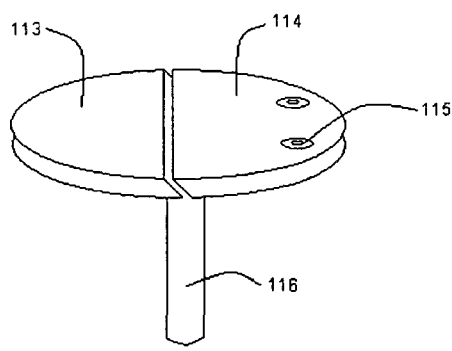
FIG. 37 is a perspective diagram of another embodiment of the cranial fixation device in a retracted position.
Figure 38:
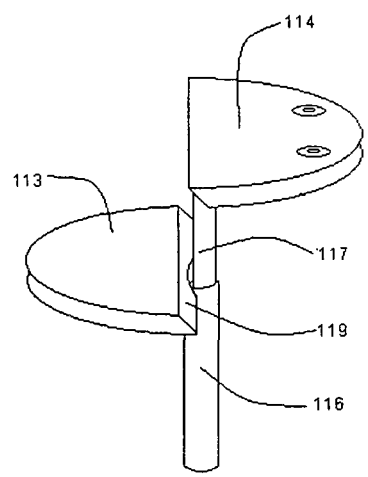
FIG. 38 is a perspective diagram of the device seen in FIG. 37 in a partially extended position.
Figure 39:
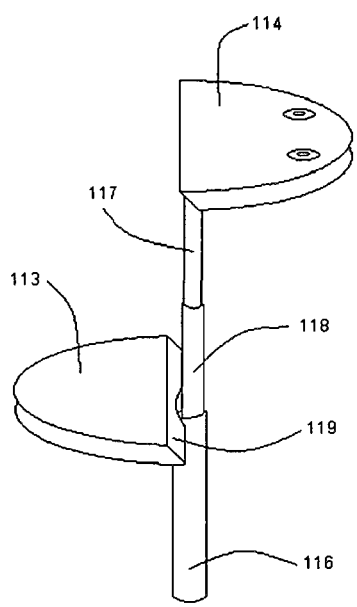
FIG. 39 is a perspective diagram of the device seen in FIG. 37 in a completely extended position.

In another embodiment, the cranial fixation device as shown in FIGS. 37 and 38 comprises a head 113 with an extension 116 and a head 114 with an extension 117. The extensions 116 and 117 are telescopic and allow for inward or outward movement of the heads relative to each other. The medial edges of the heads 113 and 114 are sloped 119 and overlap each other when the heads are approximated, thereby not allowing the head 114 to move inward beyond the head 113. The head 114 has holes 115 which allow placement of screws attaching the head to the bone flap and the head 113 rests on the outer surface of the skull. FIG. 37 shows the telescopic extensions in a compressed position whereby extension 117 is contained inside the extension 116 and FIG. 38 shows the extensions 116 and 117 in a distracted position. FIG. 39 illustrates another embodiment of the cranial fixation device with an intermediate telescopic component 118 which allows the two heads attached to their respective bone flap and skull to move outwards further if needed to accommodate an increase in intracranial pressure or brain swelling.

Figure 40:
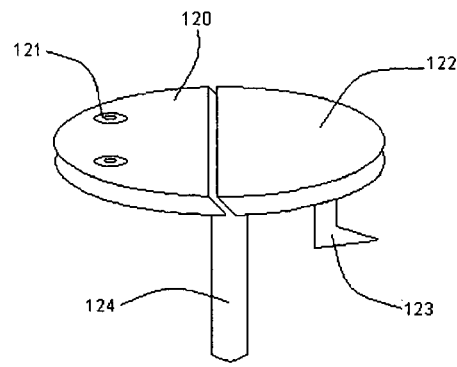
FIG. 40 is a perspective diagram of another embodiment of the cranial fixation device in a retracted position.
Figure 41:
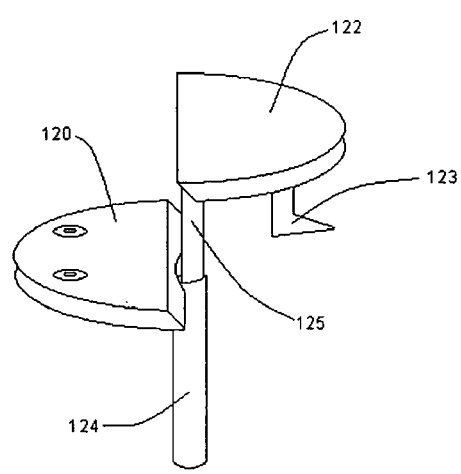
FIG. 41 is a perspective diagram of the device seen in FIG. 40 in an extended position.

In another embodiment, the cranial fixation device as shown in FIGS. 40 and 41 comprises a head 120 with an extension 124 and a head 122 with an extension 125. The extensions 124 and 125 are telescopic and allow for inward or outward movement of the heads relative to each other. The head 120 has holes 121 which allow placement of screws attaching the head to the skull and the head 122 has a clamp 123 that attaches to the dipole of the bone flap and the head 122 rests on the outer surface of the bone flap. FIG. 40 shows the telescopic extensions in a compressed position whereby extension 125 is contained inside the extension 124 and FIG. 41 shows the extensions 124 and 125 in a distracted position.

Figure 42:
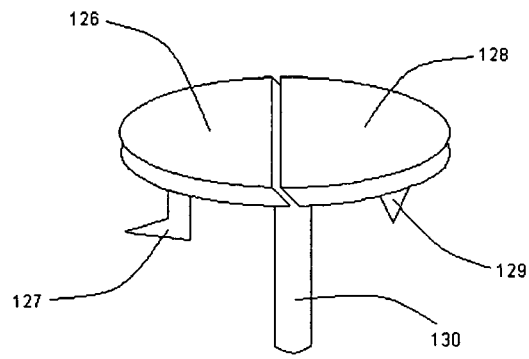
FIG. 42 is a perspective diagram of another embodiment of the cranial fixation device in a retracted position.
Figure 43:
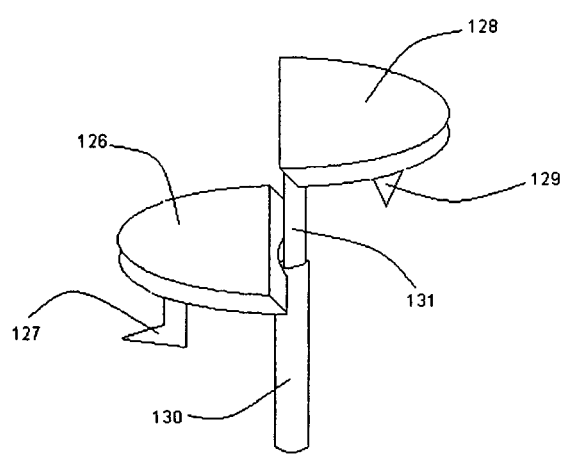
FIG. 43 is a perspective diagram of the device seen in FIG. 42 in an extended position.
Figure 44:
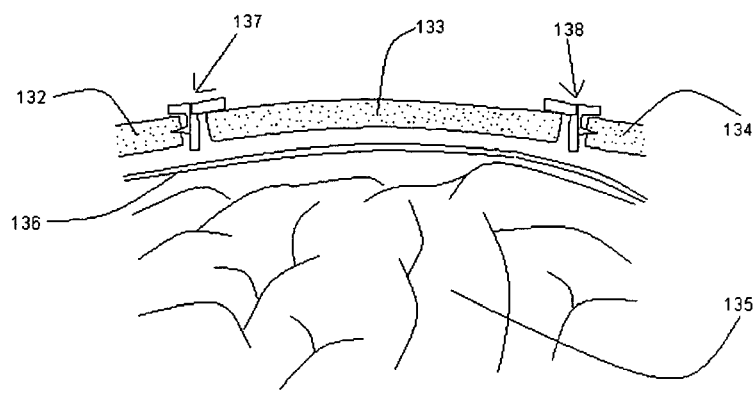
FIG. 44 is a schematic diagram of the cranial fixation device seen in FIG. 42 in a retracted position attached to the skull and bone flap.
Figure 45:
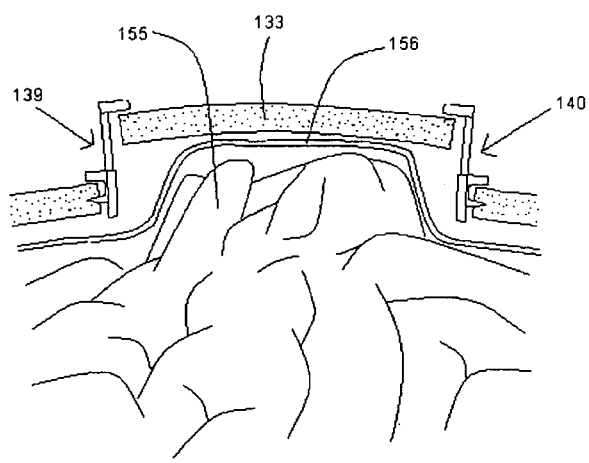
FIG. 45 is a schematic diagram of the device as seen in FIG. 43 in an extended position attached to the skull and bone flap.

In another embodiment, the cranial fixation device as shown in FIGS. 42 and 43 comprises a head 126 with an extension 130 and a head 128 with an extension 131. The extensions 130 and 131 are telescopic and allow for inward or outward movement of the heads relative to each other. The head 126 has a clamp 127 that secures the head to the skull and the head 128 has spikes 129 that attach to the bone flap. FIG. 42 shows the telescopic extensions in a compressed position whereby extension 131 is contained inside the extension 130 and FIG. 43 shows the extensions 131 and 130 in a distracted position. The method for cranial bone flap fixation with the device in FIGS. 42 and 43 is illustrated in FIGS. 44 and 45. FIG. 44 illustrates the cranial fixation devices 137 and 138 in place attached to the outer surface of the bone flap 133 and the skull 132 and 134. The brain 135 and dura 136 are shown in their normal position. Typically two or more of the cranial fixation devices would be placed to fixate the bone flap 133 to the skull 132 and 134 with the cranial fixation device telescopes in a retracted position approximating the bone flap to the skull. As shown in FIG. 45, with the development of brain swelling or an increase in intracranial pressure from a hemorrhage, the brain 155 and dura 156 push against the bone flap 133. The pressure on the bone flap places the cranial fixation device 139 and 140 telescopes in an extended position thereby allowing the bone flap to move outwards and accommodate the brain swelling.

Figure 46:
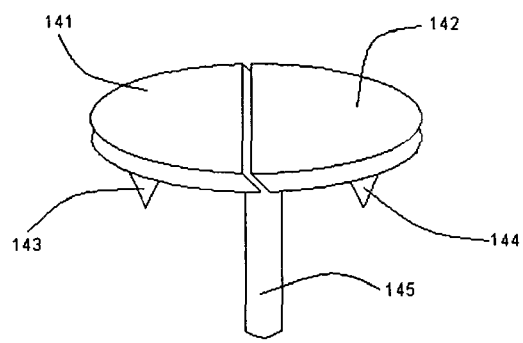
FIG. 46 is a perspective diagram of another embodiment of the cranial fixation device in a retracted position.
Figure 47:
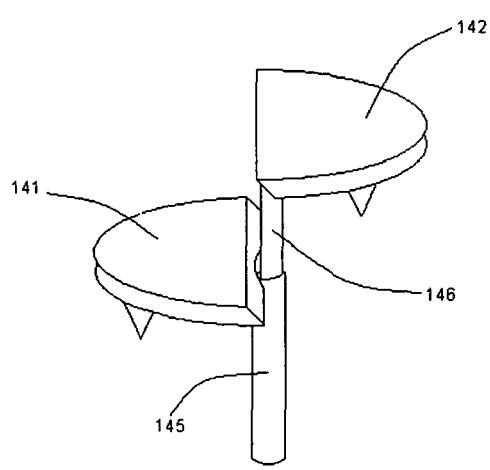
FIG. 47 is a perspective diagram of the device seen in FIG. 46 in an extended position.

In another embodiment of the cranial fixation device as shown in FIGS. 46 and 47, the head 141 comprises an extension 145 and the head 142 comprises an extension 146. The extensions 145 and 146 are telescopic and allow for inward or outward movement of the heads relative to each other. The heads 141 and 142 also comprise of spikes 143 and 144 that attach to the skull and bone flap respectively. FIG. 46 shows the telescopic extensions in a compressed position whereby extension 146 is contained inside the extension 145 and FIG. 47 shows the extensions 145 and 146 in a distracted position.

Figure 48:
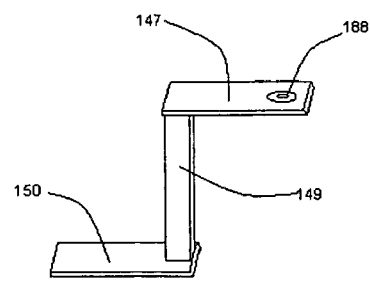
FIG. 48 is a perspective diagram of another embodiment of the cranial fixation device in a retracted position.
Figure 49:
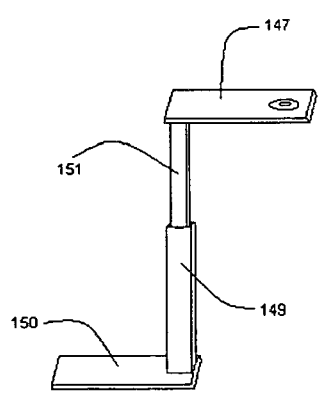
FIG. 49 is a perspective diagram of the device seen in FIG. 48 in an extended position.
Figure 50:
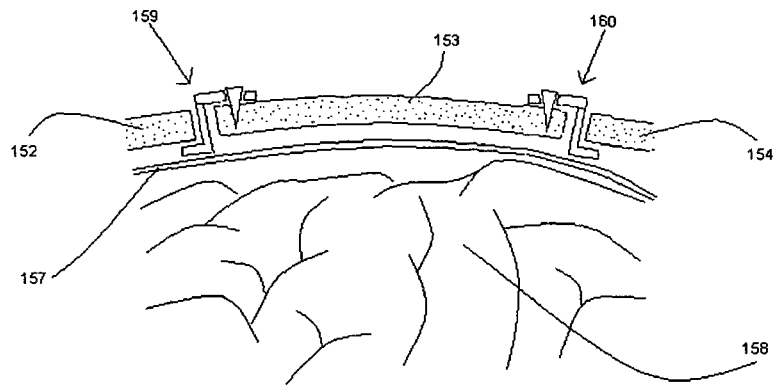
FIG. 50 is a schematic diagram of the cranial fixation device seen in FIG. 48 in a retracted position attached to the skull and bone flap.
Figure 51:
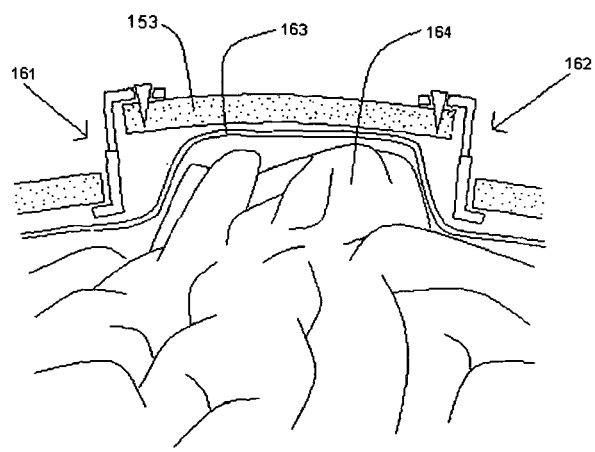
FIG. 51 is a schematic diagram of the device as seen in FIG. 49 in an extended position attached to the skull and bone flap.

While the abovementioned cranial fixation device heads are positioned on the outer surface of the skull and bone flap, in other embodiments one head is positioned on the outer surface of the skull and/or bone flap and the other head is positioned on the inner surface. The head shapes can be rectangular or circular. As shown in FIGS. 48 and 49 the head 147 rests on the outer surface of the bone flap and comprises a hole 188 for placement of a screw and a telescopic extension 151. The head 150 is positioned on the inner surface of the skull and comprises a telescopic housing extension 149. FIG. 48 shows the telescopic extensions in a compressed position whereby extension 151 is contained inside the extension 149 and FIG. 47 shows the extensions 149 and 151 in a distracted position. The method for cranial bone flap fixation with the device in FIGS. 48 and 49 is illustrated in FIGS. 50 and 51. FIG. 50 illustrates the cranial fixation devices 159 and 160 in place attached to the outer surface of the bone flap 153 with screws and the inner surface of the skull 152 and 154. The brain 158 and dura 157 are shown in their normal position. Typically two or more of the cranial fixation devices would be placed to fixate the bone flap 153 to the skull 152 and 154 with the cranial fixation device telescopes in a retracted position approximating the bone flap to the skull. As shown in FIG. 51, with the development of brain swelling or an increase in intracranial pressure from a hemorrhage, the swollen brain 164 and dura 163 push against the bone flap 153. The pressure on the bone flap places the cranial fixation device 161 and 162 telescopes in an extended position thereby allowing the bone flap to move outwards and accommodate the brain swelling.

Figure 52:
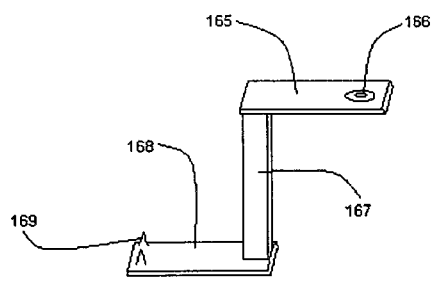
FIG. 52 is a perspective diagram of another embodiment of the cranial fixation device in a retracted position.
Figure 53:
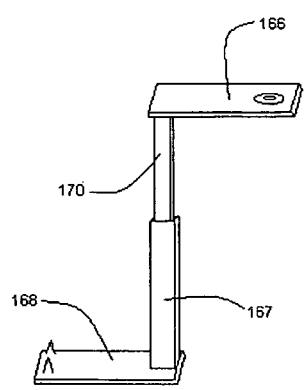
FIG. 53 is a perspective diagram of the device seen in FIG. 52 in an extended position.

In another embodiment of the cranial fixation device as shown in FIGS. 52 and 53 the head 165 rests on the outer surface of the bone flap and comprises a hole 166 for placement of a screw and a telescopic extension 170. The head 168 is attached to the Inner surface of the skull with spikes 169 and comprises a telescopic housing extension 167. FIG. 52 shows the telescopic extensions in a compressed position whereby extension 170 is contained inside the extension 167 and FIG. 53 shows the extensions 167 and 170 in a distracted position.

Figure 54:
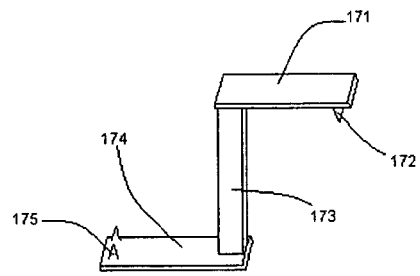
FIG. 54 is a perspective diagram of another embodiment of the cranial fixation device in a retracted position.
Figure 55:
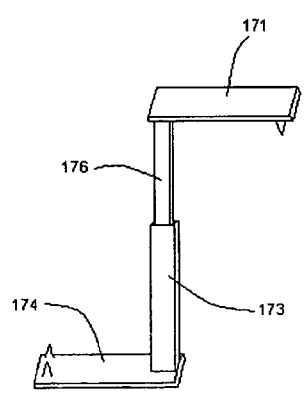
FIG. 55 is a perspective diagram of the device seen in FIG. 54 in an extended position.
Figure 56:
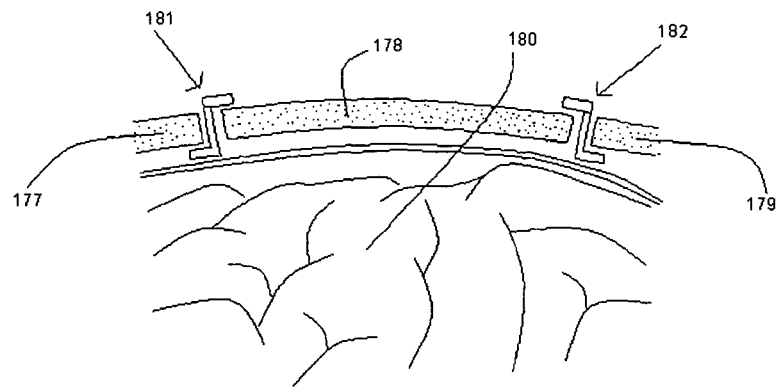
FIG. 56 is a schematic diagram of the cranial fixation device seen in FIG. 54 in a retracted position attached to the skull and bone flap.
Figure 57:
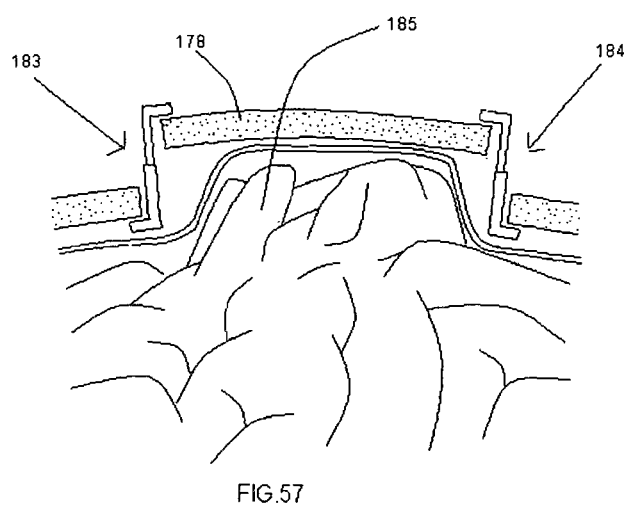
FIG. 57 is a schematic diagram of the device as seen in FIG. 55 in an extended position attached to the skull and bone flap.

In another embodiment of the cranial fixation device as shown in FIGS. 54 and 55 the head 171 is attached to the outer surface of the bone flap with spikes 172 and comprises a telescopic extension 176. The head 174 is attached to the Inner surface of the skull with spikes 175 and comprises a telescopic housing extension 173. FIG. 54 shows the telescopic extensions in a compressed position whereby extension 176 is contained inside the extension 173 and FIG. 55 shows the extensions 173 and 176 in a distracted position. The method for cranial bone flap fixation with the device in FIGS. 54 and 55 is illustrated in FIGS. 56 and 57. FIG. 56 illustrates the cranial fixation devices 181 and 182 in place attached to the outer surface of the bone flap 178 and the inner surface of the skull 77 and 179. The brain 180 is shown in its normal position. Typically two or more of the cranial fixation devices would be placed to fixate the bone flap 178 to the skull 177 and 179 with the cranial fixation device telescopes in a retracted position approximating the bone flap to the skull. As shown in FIG. 57, with the development of brain swelling or an increase in Intracranial pressure from a hemorrhage, the swollen brain 185 pushes against the bone flap 178. The pressure on the bone flap places the cranial fixation device 183 and 184 telescopes in an extended position thereby allowing the bone flap to move outwards and accommodate the brain swelling.

Figure 58:
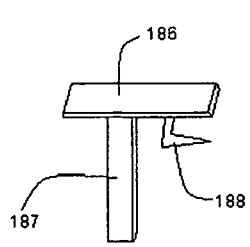
FIG. 58 is a perspective diagram of another embodiment of the cranial fixation device in a retracted position.
Figure 59:
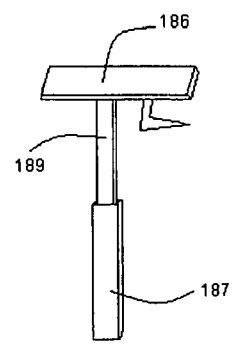
FIG. 59 is a perspective diagram of the device seen in FIG. 58 in an extended position.

In another embodiment of the cranial fixation device as shown in FIGS. 58 and 59, the head 186 rests on the outer surface of the bone flap and skull. The head 186 has a clamp 188 at one end and a telescopic extension 187 in the center that resides in the burr hole defect. The clamp end of the head attaches to the bone flap and the other head end rests on the outer surface of the skull. FIG. 58 shows the telescopic extensions in a compressed position whereby extension 189 is contained inside the extension 187 and FIG. 59 shows the extensions 187 and 189 in a distracted position.

Figure 60:
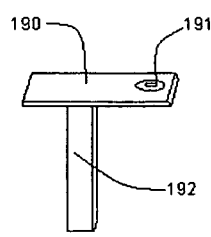
FIG. 60 is a perspective diagram of another embodiment of the cranial fixation device in a retracted position.
Figure 61:
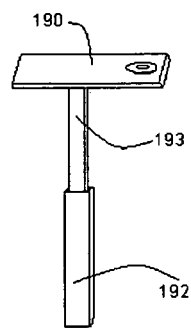
FIG. 61 is a perspective diagram of the device seen in FIG. 60 in an extended position.

In another embodiment of the cranial fixation device as shown in FIGS. 60 and 61, the head 190 rests on the outer surface of the bone flap and skull. The head 190 has a hole 191 at one end and a telescopic extension 192 in the center that resides in the burr hole defect. The screw hole 191 end of the head attaches to the bone flap and the other head end rests on the outer surface of the skull. FIG. 60 shows the telescopic extensions in a compressed position whereby extension 193 is contained inside the extension 192 and FIG. 61 shows the extensions 192 and 193 in a distracted position.

Figure 62:
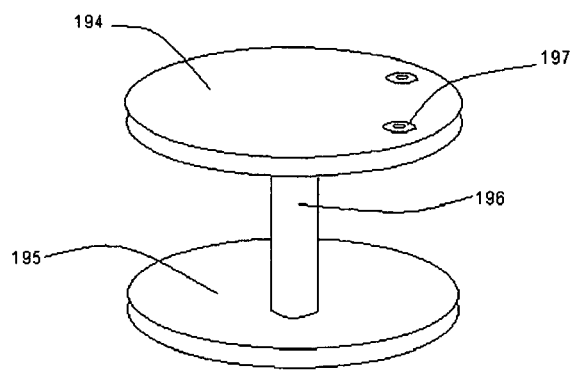
FIG. 62 is a perspective diagram of another embodiment of the cranial fixation device in a retracted position.
Figure 63:
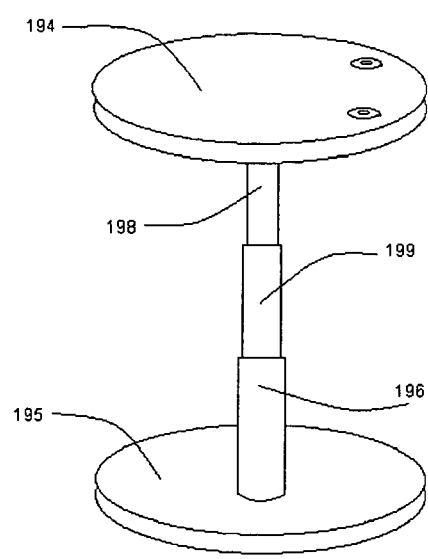
FIG. 63 is a perspective diagram of the device seen in FIG. 62 in an extended position.

In another embodiment of the cranial fixation device as shown in FIGS. 62 and 63, the device comprises of a head 194 and a head 195 connected with a telescopic portion 196. The head 194 resting on the outer surface of the bone flap and skull also comprising of holes 197 for screw placement. The side of the head 194 with screw holes 197 is secured to the bone flap and the opposing side of the head 194 rests on the skull. The head 195 rests on the inner surface of the skull and bone flap and the telescopic portion 196 is positioned in the skull defect. The telescopic portion 196 also comprises of extensions 199 and 198 that allow outward movement of the head 194 secured at one end to the bone flap as shown in FIG. 63.

Figure 64:
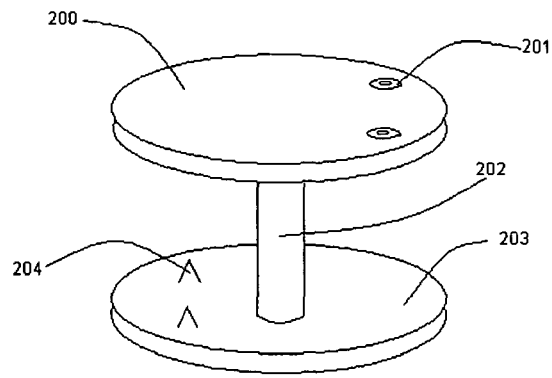
FIG. 64 is a perspective diagram of another embodiment of the cranial fixation device in a retracted position.
Figure 65:
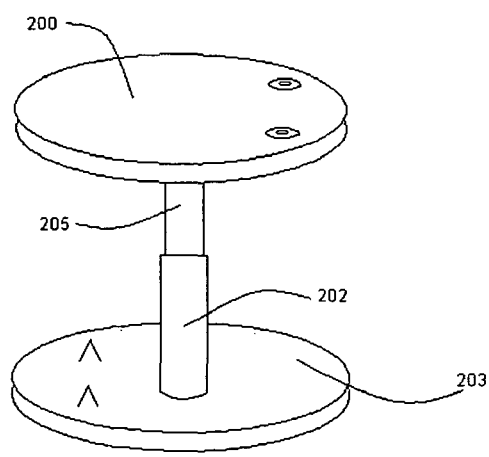
FIG. 65 is a perspective diagram of the device seen in FIG. 64 in an extended position.
Figure 66:
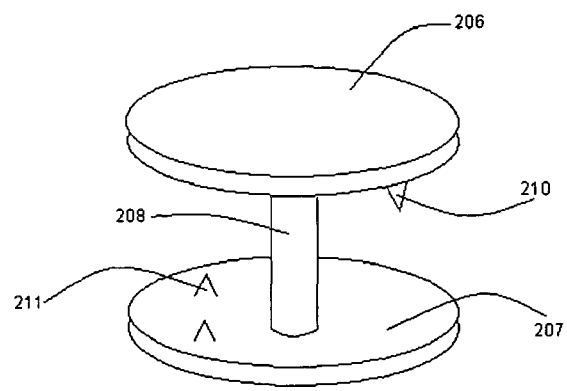
FIG. 66 is a perspective diagram of another embodiment of the cranial fixation device in a retracted position.

In another embodiment of the cranial fixation device as shown in FIGS. 64 and 66, the device comprises of a head 200 and a head 203 connected with a telescopic portion 202. The head 200 resting on the outer surface of the bone flap and skull also comprising of holes 201 for screw placement. The side of the head 200 with screw holes 201 is secured to the bone flap and the opposing side of the head 200 rests on the skull. The head 203 rests on the inner surface of the skull and bone flap and the telescopic portion 196 is positioned in the skull burr hole opening. The side of the head 203 towards the skull comprises of spikes 204 for attachment to the inner surface of the skull. The telescopic portion 202 also comprises of extension 205 that allows outward movement of the head 200 secured at one end to the bone flap as shown in FIG. 65.

Figure 67:
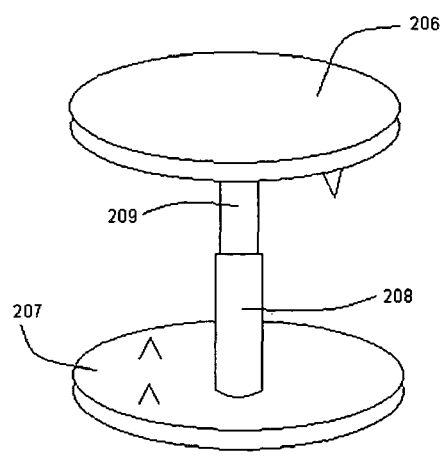
FIG. 67 is a perspective diagram of the device seen in FIG. 66 in an extended position.
Figure 68:
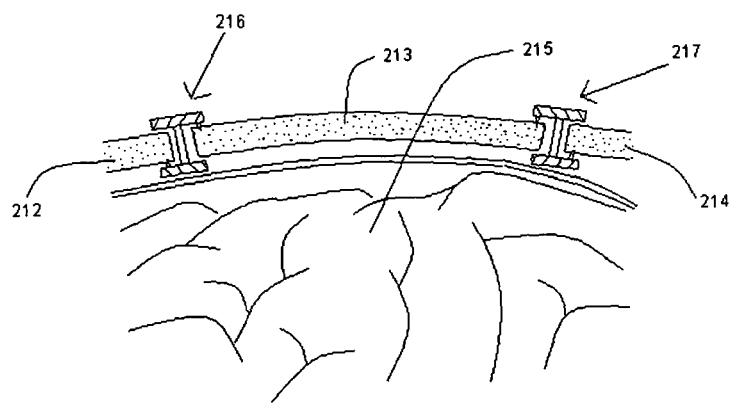
FIG. 68 is a schematic diagram of the cranial fixation device seen in FIG. 66 in a retracted position attached to the skull and bone flap.
Figure 69:
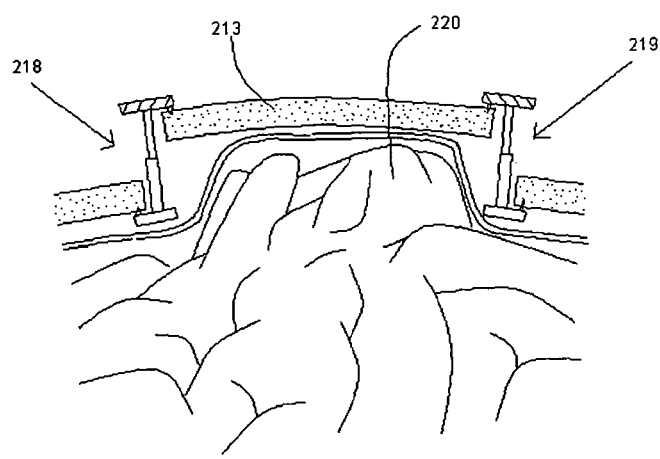
FIG. 69 is a schematic diagram of the device as seen in FIG. 67 in an extended position attached to the skull and bone flap.

In another embodiment of the cranial fixation device as shown in FIGS. 66 and 67, the device comprises of a head 206 and a head 207 connected with a telescopic portion 208. The head 200 resting on the outer surface of the bone flap and skull also comprising of spikes 210 on the side of the head secured to the bone flap and the opposing side of the head 200 rests on the skull. The head 207 rests on the inner surface of the skull and bone flap and the telescopic portion 196 is positioned in the skull defect. The side of the head 207 towards the skull comprises of spikes 211. The telescopic portion 208 also comprises of extension 209 that allows outward movement of the head 206 as shown in FIG. 67. The method for cranial bone flap fixation with the device in FIGS. 66 and 67 is illustrated in FIGS. 68 and 69. FIG. 68 illustrates the cranial fixation devices 216 and 217 in place attached to the outer and inner surface of the bone flap 213 and the skull 212 and 214 respectively. The brain 215 is shown in its normal position. Typically two or more of the cranial fixation devices would be placed to fixate the bone flap 213 to the skull 212 and 214 with the cranial fixation device telescopes in a retracted position approximating the bone flap to the skull. As shown in FIG. 69, with the development of brain swelling or an increase in intracranial pressure from a hemorrhage, the swollen, brain 220 pushes against the bone flap 213. The pressure on the bone flap places the cranial fixation device 218 and 219 telescopes in, an extended position thereby allowing the bone flap to move outwards and accommodate the brain swelling.

Figure 70:
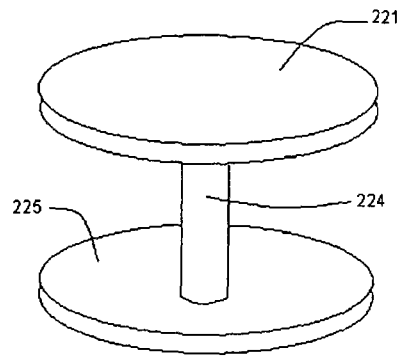
FIG. 70 is a perspective diagram of another embodiment of the cranial fixation device in a retracted position.
Figure 71:
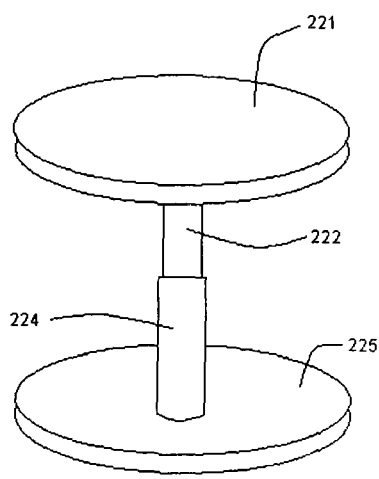
FIG. 71 is a perspective diagram of the device seen in FIG. 70 in a partially extended position.
Figure 72:
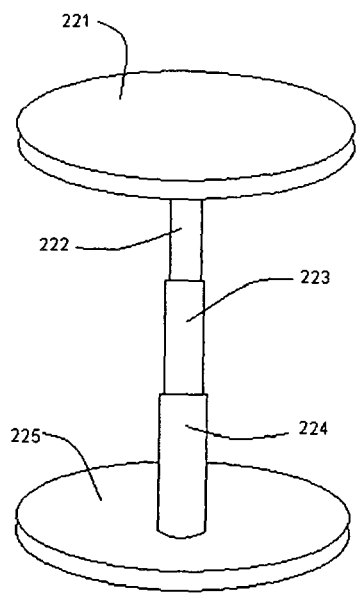
FIG. 72 is a perspective diagram of the device seen in FIG. 70 in a completely extended position.
Figure 73:
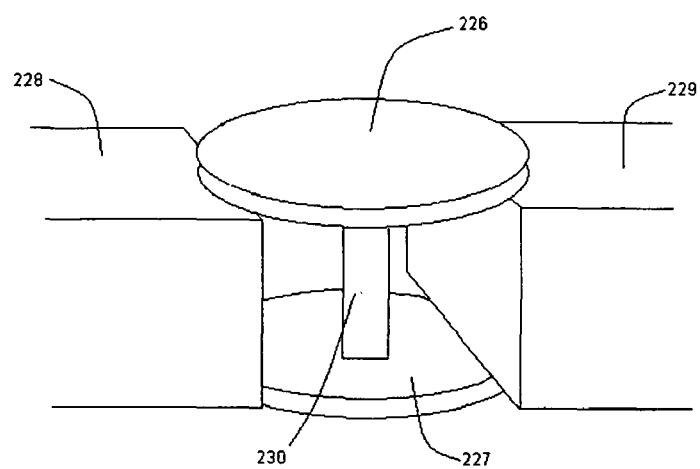
FIG. 73 is a partial schematic view of the cranial fixation device seen in FIG. 70 attached to the bone flap and skull in a retracted position.

In another embodiment of the cranial fixation device as shown in FIGS. 70-72, the head 221 rests on the outer surface of the bone flap and skull and comprises an extension 222. The head 225 rests on the inner surface of the bone flap and skull and comprises a hollow extension 224. The extensions 222 and 224 are telescopically connected by an intermediary hollow extension 223. FIG. 72 illustrates the device in a distracted position with telescopic extensions 222, 223, and 224. FIG. 71 illustrates the device in a partially distracted position with the telescopic extensions 222 and 224. The intermediate extension 223 has telescoped inside the extension 224. FIG. 70 illustrates the device in a completely retracted position with the intermediate extension 223 and head extension 222 telescoped inside extension 224, thereby bringing the heads 221 and 225 closer together. FIG. 73 illustrates the cranial fixation device in place with head 226 resting on the outer surface of the bone flap 228 and skull 229. The head 227 rests on the inner surface of the bone flap 228 and skull 229. The two heads 226 and 227 are connected by the telescopic extension 230 residing in the burr hole defect between the bone flap 228 and skull 229. Various telescopic extension locking mechanisms are illustrated in FIGS. 74-82.

Figure 74:
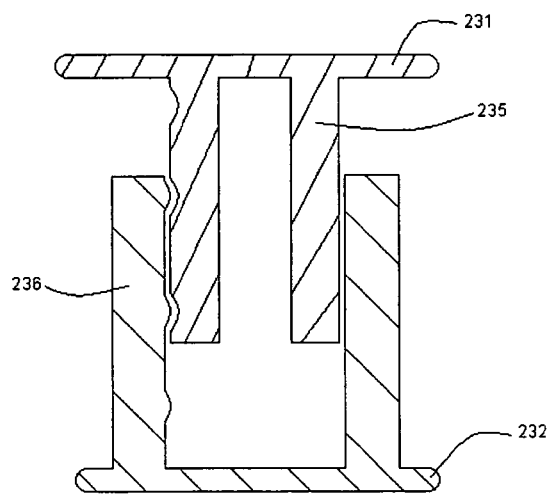
FIG. 74 is a cross-sectional side view of another embodiment of the cranial fixation device in a retracted position.
Figure 75:
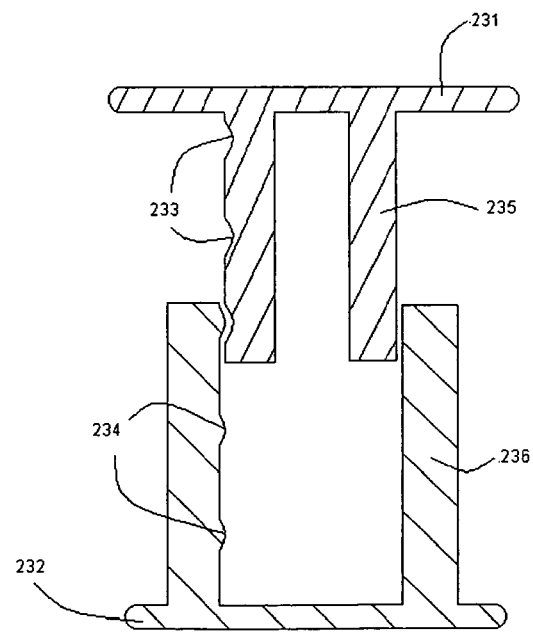
FIG. 75 is a cross-sectional view of the device seen in FIG. 74 in an extended position.

In another embodiment of the cranial fixation device as shown in FIGS. 74 and 75, the head 231 comprises a telescopic extension 235 and the head 232 comprises a telescopic extension 236. The extension 236 contains ridges 234 that engage with corresponding recesses 233 in extension 235. FIG. 74 shows the telescopic extensions 235 and 236 in a partially retracted position and FIG. 75 shows the telescopic extensions in an extended position.

Figure 76:
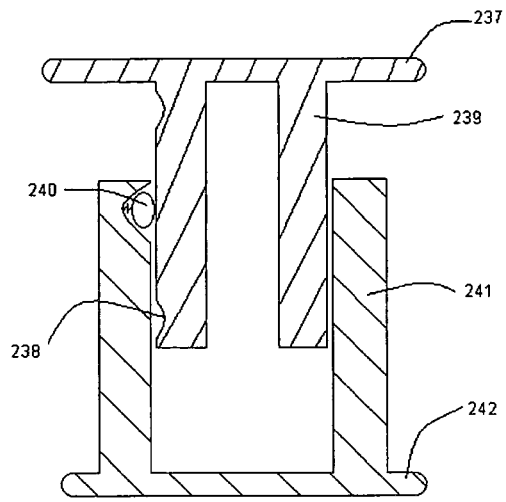
FIG. 76 is a cross-sectional side view of another embodiment of the cranial fixation device in a retracted position.
Figure 77:
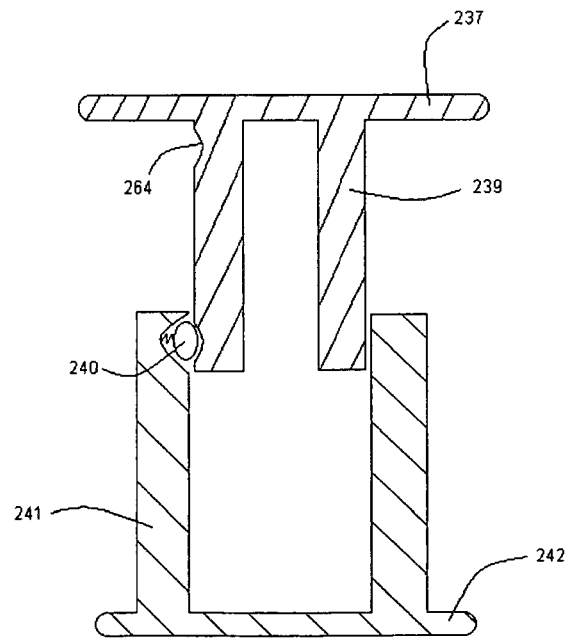
FIG. 77 is a cross-sectional view of the device seen in FIG. 76 in an extended position.

In another embodiment of the cranial fixation device as shown in FIGS. 76 and 77, the head 237 comprises a telescopic extension 239 and the head 242 comprises a telescopic extension 241. The extension 241 contains a collapsible ball 240 that engage with corresponding recesses 238 and 264 in extension 239.

Figure 78:
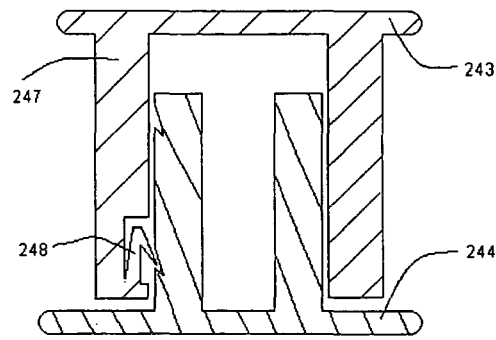
FIG. 78 is a cross-sectional side view of another embodiment of the cranial fixation device in a retracted position.
Figure 79:
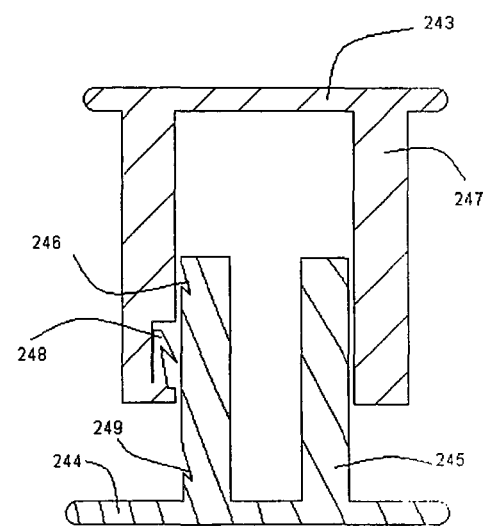
FIG. 79 is a cross-sectional view of the device seen in FIG. 78 in a partially extended position.
Figure 80:
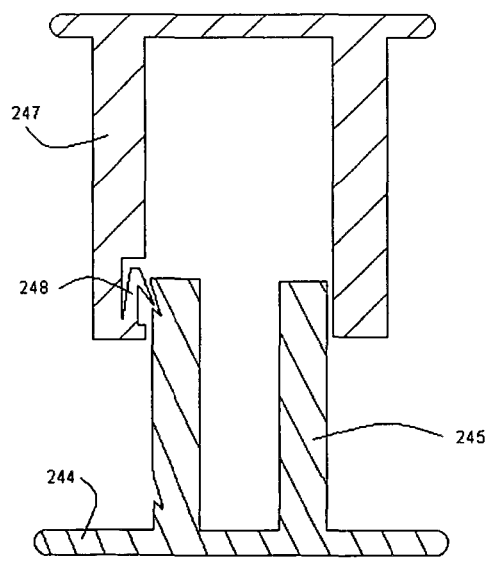
FIG. 80 is a cross-sectional view of the device seen in FIG. 78 in a completely extended position.

FIG. 76 shows the telescopic extensions 239 and 241 in a partially retracted position and FIG. 77 shows the telescopic extensions in an extended position. In another embodiment of the cranial fixation device as shown in FIGS. 78-80, the head 243 comprises a telescopic extension 247 and the head 244 comprises a telescopic extension 245. The extension 247 contains a collapsible hook 248 that engages with corresponding recesses 246 and 249 in extension 245. FIG. 78 shows the telescopic extensions 245 and 247 in a retracted position with the hook 248 engaged with the recess 249. FIG. 79 shows the telescopic extensions in a partially retracted position and FIG. 80 shows the telescopic extensions in an extended position with the hook 248 engaged with the recess 246.

Figure 81:
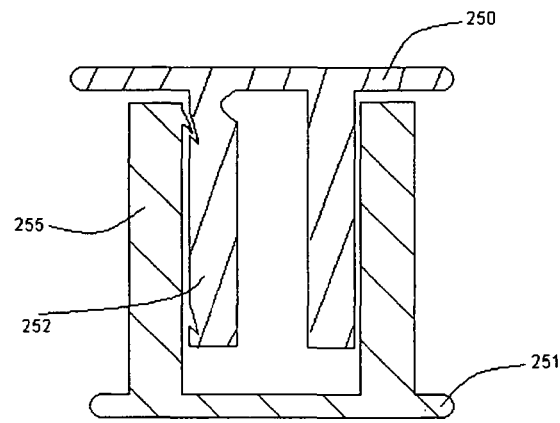
FIG. 81 is a cross-sectional side view of another embodiment of the cranial fixation device in a retracted position.
Figure 82:
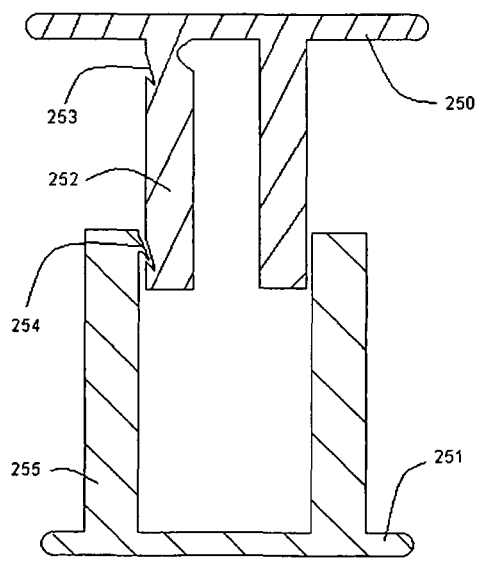
FIG. 82 is a cross-sectional view of the device seen in FIG. 81 in an extended position.

In another embodiment of the cranial fixation device as shown in FIGS. 81 and 82, the head 250 comprises a telescopic extension 252 and the head 251 comprises a telescopic extension 255. The extension 255 contains ratchet teeth 254 that engage with corresponding recesses 253 in extension 252. FIG. 81 shows the telescopic extensions 252 and 255 in a retracted position and FIG. 82 shows the telescopic extensions in an extended position.

Although several telescopic extension engaging mechanisms are described in the various embodiments, it is obvious that any variations made to the embodiments by those skilled in the art maintain the broad incentive concepts described herein.

Figure 84:
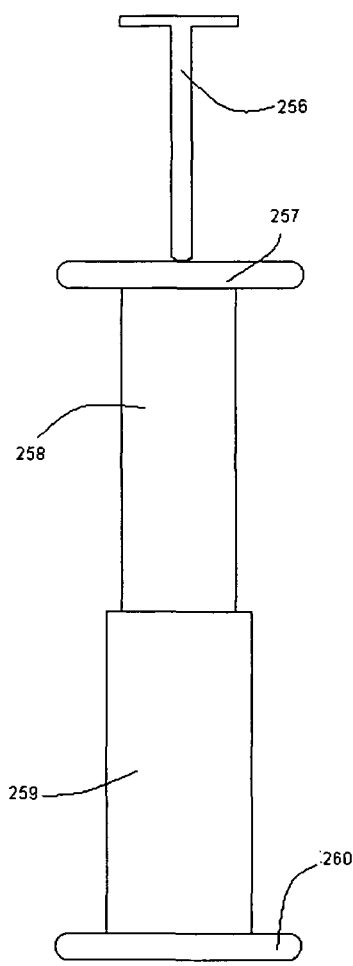
FIG. 84 is a perspective side of the device seen in FIG. 83 with the head extension removed.
Figure 83:
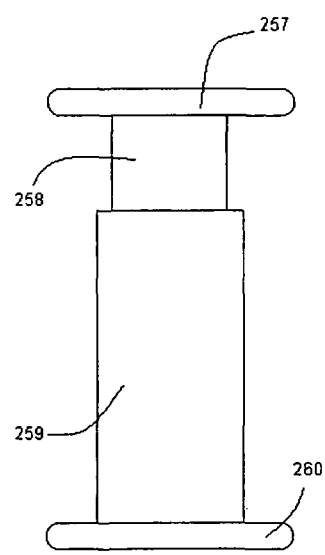
FIG. 83 is a perspective side view of another embodiment of the cranial fixation device with a removable superior head extension.

The head on the outer surface of the skull can also contain a removable extension to assist in holding and placement of the cranial fixation devices described herein. As shown in FIG. 84 the head 257 comprises a telescopic extension 258 as well as an extension 256. The head 260 comprises a telescopic extension 259. The extension 256 can be used to hold the cranial fixation device and position the head 260 under the inner surface of the bone flap and skull following the craniotomy. Once the head 257 is positioned on the outer surface of the skull and bone flap, the extension 256 can be snapped off either manually or with a cutting instrument. The cranial fixation device of FIG. 4 with the extension 256 removed is shown in FIG. 83.

Figure 85:
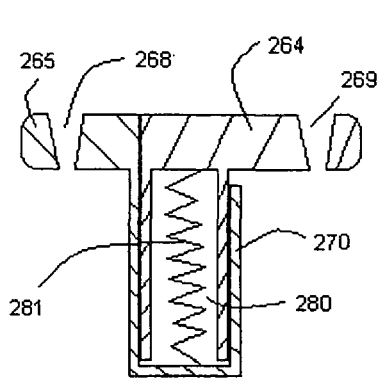
FIG. 85 is a cross-sectional side view of another embodiment of the cranial fixation device in a retracted position.
Figure 86:
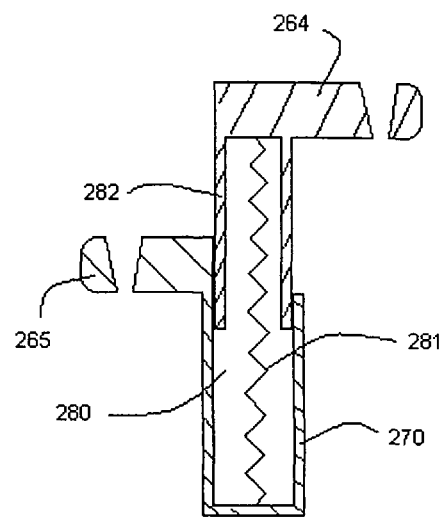
FIG. 86 is a cross-sectional view of the device in FIG. 85 in an extended position.
Figure 87:
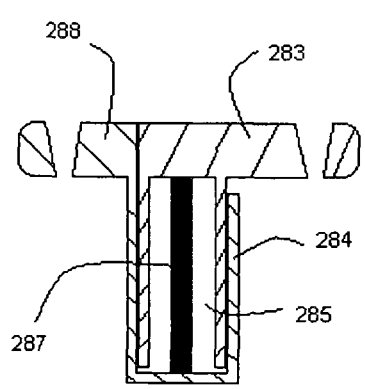
FIG. 87 is a cross-sectional view of another embodiment of the cranial fixation device in a retracted position.
Figure 88:
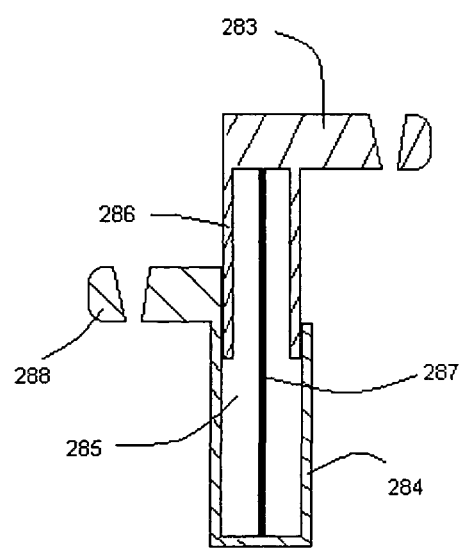
FIG. 88 is a cross-sectional view of the device in FIG. 87 in an extended position.

In alternate embodiments, the heads or telescopic components can be connected with a flexible material like a spring or an elastomer which retracts the telescopic extensions thereby positioning the bone flap down towards the skull once the ICP has reduced to a normal level. As shown in FIGS. 85 and 86, the two heads 264 and 265 contain telescopic extensions 270 and 282 with bone screw holes 268 and 269. The head 264 is attached to a spring 281 that is housed in the hollow component 280 of the telescopic extension and is also attached to the telescopic extension 270. In the current embodiment the spring is shown residing inside the telescopic extensions but in other embodiments it can be placed outside the telescopic extensions. With normalization of the intracranial pressure the spring 281 retracts the heads and telescopic extensions to approximate the two heads together as shown in FIG. 85. With an increase in intracranial pressure the head 264 connected to the bone flap is pushed outwards and places the telescopic extensions in an extended position as shown in FIG. 86. FIGS. 87 and 88 illustrate another embodiment of the fixation device with heads 283 and 288 and telescopic extensions 284 and 286 with an elastomeric band 287 that is housed in the hollow portion 285 of the telescopic extensions. FIG. 87 shows the retracted position of the telescopes with heads approximated and FIG. 88 shows the extended position of the telescopic extensions.

The normal intracranial pressure is less than 20 mm-Hg and with any brain swelling or hemorrhage the intracranial pressure can increase to greater than 20 mm Hg. With an increase in the intracranial pressure above the normal range, the cranial fixation devices are designed to disengage the locking mechanism and place the telescopic extensions into an extended position from a retracted position and therefore place the two heads apart, thereby allowing the bone flap to move outwards from the skull in a constrained manner and accommodate the higher intracranial pressure. Once the intracranial pressure reaches below 20 mm Hg again the telescopic extensions retract and position the bone flap downwards to the skull level.

In the various embodiments described herein the preferred head configuration is either circular or semi-circular coming together in a circular shape when the telescopic extensions are in a compressed position. The circular shape covers the burr hole skull defect. Other head shapes can include oval, rectangular, square, semi-oval, C-shape, L-shape, T-shape, X-shape, Y-shape, Z-shape, fan shaped or any other configuration able to connect the skull to the bone flap. Similarly, the telescopic configurations described are either cylindrical or rectangular and hollow designed to fit into the burr hole or skull opening. Other telescopic configurations could be partially solid, tapered. V-shaped or any other configuration that fit's the skull opening. The cranial fixation device can be made of titanium or titanium alloy for MRI imaging compatibility. It could also be made of a bioresorbable (polyesters, poly amino adds, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft, or xenograft bone that is absorbed by the body over time once the bone flap has fused with the skull. Alternatively, it could made of a radiolucent material like polyetheretherketone (PEEK) or polyaryletherketone (PEAK), high molecular weight polyethylene, carbon fiber, polyurethane, plastic, or a combination of plastic and metal to reduce CT and MRI imaging artifact. The cranial fixation device discussed herein can be of unitary construction, such that the heads and telescopic portions can be integral or formed from a single piece material. Alternative embodiments contemplate that the components of the cranial fixation device can be non-Integral, and can be attached to and/or coupled to other components of the device. The thickness of the heads can range from 3 mm to 20 mm. The size of the head can range from 6 mm to 40 mm. The length of the telescopic portion in a retracted position can range from 5 mm to 20 mm and in an extended position can range from 10 mm to 60 mm. The length of the screws can range from 4 mm to 20 mm. While the above-mentioned size range of the device components reflects the preferred embodiments, other embodiments can comprise of head, telescope, and screw sizes outside of the aforementioned ranges. The angulations of the telescopic component in the preferred embodiment are 90 degrees relative to the heads but could any other angle from perpendicular to parallel to the head.

While the invention and methodology described herein along with the illustrations is specific, it is understood that the invention is not limited to the embodiments disclosed. Numerous modifications, rearrangements, and substitutions can be made with those skilled in the art without departing from the spirit of the invention as set forth and defined herein.

I claim:

1. A cranial fixation device for fixing a bone flap to a skull, the device comprising at least a first and a second operatively connected engaging portions, wherein the first portion is configured to be attached to the skull with a first top segment and the second portion is configured to be attached to the bone flap with a second top segment, the device includes a third portion that is a third telescopic component residing between a first telescopic component of the first portion and a second telescopic component of the second portion and not directly connected to the first top segment and the second top segment, wherein the device is moveable between a first position, a second position, and a third position to accommodate changes in intracranial pressure, wherein the device includes at least one locking mechanism for preventing the bone flap from moving inward below the skull level, wherein the at least one locking mechanism is handled by edges of the first top segment of the first portion and of the second top segment of the second portion that are sloped adjacent a central axis of the device and overlap each other when the first top segment and the second top segment are approximated to not allow the second portion from moving inward beyond the first portion, and wherein the first telescopic component is connected to the sloped edge of the first top segment and the second telescopic component is connected to the sloped edge of the second top segment.

2. The cranial fixation device of claim 1, wherein the first and second portions engage telescopically.

3. The device of claim 1, wherein the locking mechanism comprises at least one ridge of the second and third portions of the device, and at least one corresponding recess of the first portion.

4. The device of claim 3, wherein the locking mechanism comprises two recesses in the first portion, wherein a first recess is located near a bottom end of the first portion, and a second recess is located near a top end of the first portion.

5. A cranial fixation device for fixing a bone flap to a skull, the device comprising three operatively engaging portions having a common boundary, wherein the device is adapted to provide constrained outward movement of the bone flap responsive to changes in an intracranial pressure without allowing the bone flap to move inwardly below a skull level, wherein a first portion is attachable to the skull with a first to segment, a second portion is attachable to the bone flap with a second top segment, and a third portion that is a telescopic component residing between a first telescopic component of the first portion and a second telescopic component of the second portion and not directly connected to the first top segment and the second top segment, and wherein the device includes at least one locking mechanism for preventing the bone flap from moving inward below the skull level, and wherein the locking mechanism is handled by edges of the first top segment of the first portion and of the second top segment of the second portion that are sloped adjacent a central axis of the device and overlap each other when the first top segment and of the second top segment are approximated to not allow the second portion from moving inward beyond the first portion, and wherein the first telescopic component is connected to the sloped edge of the first top segment and the second telescopic component is connected to the sloped edge of the second top segment.

6. The device of claim 5, wherein the first, second and third portions are disposable in a burr hole, wherein the second portion comprises at least one upwardly extension and the second portion is adapted to move between retracted positions and extended positions in response to variations of the intracranial pressure.

7. The device of claim 6, wherein the third portion is adapted to move between retracted positions and extended positions in response to variations of the intracranial pressure.

8. The device of claim 5, wherein the three portions are telescopically engaging.

9. The device of claim 5, wherein the first and second portions are adapted to releasably attach to the skull and the bone flap.

10. The device of claim 9, wherein the first portion is configured to be releasably engaging the skull by at least one screw and wherein the second portion is configured to be releasably engaging the bone flap by at least one screw.

11. The device of claim 5, wherein the at least one locking mechanism comprises at least one ridge of the second and third portions of the device, and at least one corresponding recess of the first portion.

12. The device of claim 5, wherein the three operatively engaging portions are sloped to overlap with other portions when the portions are approximated to prevent any portions from moving downwardly beyond the other portion.

13. The device of claim 12, wherein the three engaging portions engage the at least one ridge disposed inside the at least one recess in the extended position to prevent any of the second and third portions from pulling out in the extended position.

14. A cranial fixation device comprising a skull portion including an essentially horizontal top segment having a top surface, a bottom surface, an inner edge, an outer edge, and a first receiving member extending downwardly from the top segment, wherein the skull portion is attachable to a skull with the essentially horizontal top segment, a bone flap portion including an essentially horizontal top bone flap segment having a top bone flap surface, a bottom bone flap surface, an inner bone flap edge, an outer bone flap edge, wherein the bone flap portion is attachable to a bone flap of the skull with the essentially horizontal to bone flap segment, a bone flap telescoping member extending downwardly from the top bone flap segment, and a third portion that is a telescopic component residing between the first receiving member of the skull portion and the bone flap telescoping member of the bone flap portion and having a second receiving member and not directly connected to the essentially horizontal top segment and the horizontal top bone flap segment, wherein the bone flap telescoping member is slidably connected to the second receiving member for reacting to changes in intracranial pressure, and the third portion is slidably connected to the first receiving member for reacting to changes in intracranial pressure, wherein the device includes at least one locking mechanism for preventing the bone flap portion from moving inward below a skull level, and wherein the locking mechanism is handled by the inner edge of the skull portion and the inner bone flap edge of the bone flap portion that are sloped adjacent a central axis of the device and overlap each other when the essentially horizontal top segment and the essentially horizontal to bone flap segment are approximated to not allow the bone flap portion from moving inward beyond the skull portion, and wherein the first receiving member is connected to the sloped inner edge of the essentially horizontal top segment and the bone flap telescoping member is connected to the sloped inner bone flap edge of the essentially horizontal top bone flap segment.

15. The cranial fixation device of claim 14, wherein the skull portion, the bone flap portion and the third portion are telescopically engaging.

16. The cranial fixation device of claim 14, wherein the first receiving member and the telescoping member extend from the inner edges of the skull portion and the bone flap portion.

17. The cranial fixation device of claim 14, wherein the first receiving member and the telescoping member extend from a center of the skull portion and the bone flap portion.

18. The cranial fixation device of claim 14, wherein the skull portion and the bone flap portion are selected from a group of shapes comprising essentially a half-circle, circle, partial circle, a square, and a rectangle.

19. The cranial fixation device of claim 14, wherein the locking mechanism comprises at least one ridge of the bone flap portion and the third portion, and a first recess and a second recess of the skull portion, wherein the first recess is located near a bottom end of the skull portion, and the second recess is located near a top end of the skull portion.

20. The cranial fixation device of claim 14, wherein the skull portion is configured to be releasably engaging the skull by at least one screw and the bone flap portion is configured to be releasably engaging the bone flap by at least one screw.

* * * * *